US006169387B1

(12) United States Patent
Kaib

(10) Patent No.: US 6,169,387 B1
(45) Date of Patent: Jan. 2, 2001

(54) BATTERY MANAGEMENT APPARATUS FOR PORTABLE ELECTRONIC DEVICES

(75) Inventor: Thomas E. Kaib, North Huntingdon, PA (US)

(73) Assignee: Lifecor, Inc., Pittsburgh, PA (US)

( * ) Notice: Under 35 U.S.C. 154(b), the term of this patent shall be extended for 0 days.

(21) Appl. No.: 09/361,110

(22) Filed: Jul. 26, 1999

Related U.S. Application Data

(63) Continuation-in-part of application No. 08/995,713, filed on Dec. 22, 1997, now Pat. No. 5,929,601.

(51) Int. Cl.$^7$ .......................... H01M 10/46; H01M 10/44
(52) U.S. Cl. ............................................................. 320/132
(58) Field of Search .................................. 320/113, 114, 320/115, 132, 134, 136, 149, 155

(56) References Cited

U.S. PATENT DOCUMENTS

| | | | |
|---|---|---|---|
| 4,080,558 | 3/1978 | Sullivan | 320/39 |
| 4,296,755 | 10/1981 | Judell | 128/705 |
| 4,432,375 | 2/1984 | Angel et al. | 128/705 |
| 4,473,078 | 9/1984 | Angel | 128/419 |
| 4,919,144 | 4/1990 | Vandehey | 128/705 |
| 5,225,763 | 7/1993 | Krohn et al. | 320/115 X |
| 5,306,956 * | 4/1994 | Ikeda et al. | 320/113 X |
| 5,411,537 | 5/1995 | Munshi et al. | 607/33 |
| 5,470,343 | 11/1995 | Fincke et al. | 607/5 |
| 5,483,165 * | 1/1996 | Cameron et al. | 320/DIG. 21 X |
| 5,606,242 | 2/1997 | Hull et al. | 320/106 |
| 5,619,117 * | 4/1997 | Koenck | 320/106 |
| 5,625,291 * | 4/1997 | Brink et al. | 320/131 X |
| 5,929,601 * | 7/1999 | Kaib et al. | 320/113 |

* cited by examiner

Primary Examiner—Edward H. Tso
(74) Attorney, Agent, or Firm—Buchanan Ingersoll, P.C.

(57) ABSTRACT

A battery management system can have a portable electronic device for providing electrical therapy to the body of a patient responsive to the occurrence of a treatable condition. The portable device can have a rechargeable battery, memory, data processor for determining available operating time for the portable device prior to recharging, and a display panel, or alarm, to inform the patient of, inter alia, available operating time. The portable device data processor can obtain and record data regarding the patient, the battery, and the portable device operational status. The battery management system can also include a rechargeable "smart battery," of known design, which has an integral processor and memory capable of monitoring and updating the status and condition of the battery. The portable electronic device can communicate with and update the operational characteristics stored by the smart battery. The smart battery can be recharged using an appropriate conventional recharger. The portable electronic device can include battery maintenance capabilities to perform tests on the smart battery to independently evaluate the condition thereof. The portable electronic device can also have a battery status monitoring circuit which can monitor the battery condition independently of the smart battery internal monitoring system. The portable electronic device can further include a converter-defibrillator.

35 Claims, 9 Drawing Sheets

BATTERY MANAGEMENT APPARATUS FOR PORTABLE ELECTRONIC DEVICES

RELATED PATENT APPLICATIONS

This application is a continuation-in-part application of U.S. patent application Ser. No. 08/995,713, filed Dec. 22, 1997, now U.S. Pat. No. 5,929,601 which is hereby incorporated herein by reference.

BACKGROUND OF THE INVENTION

1. Field of the Invention

The present invention relates generally to portable electronic devices which utilize batteries. More particularly, the present invention relates to portable medical devices. Still more particularly, the present invention relates to methods and apparatus for the maintenance and management of the batteries of such portable medical devices.

2. Description of the Prior Art

Battery management is a concern in any portable electronic device, but is a primary concern in portable medical devices. The need for more comprehensive battery maintenance in portable and implantable medical devices has been noted, for example, in U.S. Pat. No. 4,080,558 to Sullivan, U.S. Pat. No. 5,411,537 to Munshi, et. al., U.S. Pat. No. 5,483,165 to Cameron, et. al., and U.S. Pat. No. 5,470,343 to Fincke, et. al.

A defibrillator is a device capable of delivering a preset amount of electrical energy to a patient's heart for the purpose of terminating an arrhythmia. For portable defibrillators, batteries are used to provide the electrical energy delivered. Historically, portable defibrillator maintenance has been problematic due to insufficient means to ensure comprehensive management of the batteries. As portable medical devices are intended for relatively long-term monitoring and, in the case of portable defibrillators, intended for therapeutic shock delivery for patients at risk from sudden cardiac death due to tachyarrhythmias, a comprehensive battery management program is essential.

Historically portable defibrillator design has been concerned with ensuring that the devices function properly when needed. Problems may arise if the batteries of the defibrillators are at less than full capacity or are worn out or are accidentally taken off their chargers so that the batteries are nonfunctional.

Therefore, there is a need in the portable electronic device industry, and, in particular, in the portable medical electronic device industry to implement a comprehensive way of informing the patient, as precisely as possible, of the status of that patient's device, and particularly the status of the device battery. This status should include not only the current conditions of the device battery but also other information, such as an indication of how much time remained in which the device would be operable.

SUMMARY OF THE INVENTION

The present invention is preferably utilized in connection with a patient-worn energy delivery system for imparting electrical therapy to the body of a patient responsive to an occurrence of a treatable condition. The present invention is designed to constantly monitor and comprehensively inform the patient of the condition of the device, and particularly the condition of the device battery.

The system includes a monitor-defibrillator worn by the patient. The monitor-defibrillator monitors the patient's ECG to detect life threatening arrhythmias and delivers a cardioverting or defibrillating shock if needed. The monitor-defibrillator records system operational information and ECG signal data. Periodically the patient is required to off-load this information to a patient base station. This is accomplished when the monitor-defibrillator is connected to a patient base station at the time battery charging is initiated. Thus, the patient base station is coupled with the monitor-defibrillator for periodic battery charging, device maintenance and the offloading of data. When a monitor-defibrillator is inserted into the monitor interface connector, the patient base station retrieves battery status from the monitor. The patient base station analyzes this information and may schedule maintenance operations or patient notifications if certain conditions are met.

The primary functions performed by the patient base station are providing data communication interfaces to the various components of the system, battery pack charging and maintenance, monitor-defibrillator maintenance, monitor-defibrillator data retrieval and storage, facilitating monitor-defibrillator initialization via the physician programming console and providing visual and audible feedback for patient interactions.

The patient base station provides means to simulate the operation of various monitor-defibrillator and electrode harness hardware functions. These enable the patient base station to verify that the monitor-defibrillator and the electrode harness hardware is functioning properly.

A physician programming console is also utilized, which is an IBM PC-AT compatible computer. The physician programming console facilitates programming of the patient base station and the monitor-defibrillator. Also included is an electrode harness, worn by the patient on the chest, which contains electrodes for sensing ECG signals from the heart and large surface area electrodes for delivering therapy pulses to the heart in the event of the occurrence of a treatable arrhythmia.

The monitor-defibrillator indicates the future time or activity level remaining at which the device could operate. The apparatus considers the rates of discharge and the rates of use and the amount of energy taken out of the battery. The device also monitors the number of charge cycles on the battery, the date when the battery was installed and other pertinent information such as battery pack expiration parameters.

The monitor-defibrillator itself includes circuitry to monitor the capacity of the battery. Thus, if the monitor-defibrillator undergoes some kind of abnormality, for example, some component begins drawing more current than the normal average current of the device, the circuit will detect the abnormality and the current will trip a comparator. The comparator alerts the computer and the remaining run time of the battery pack will be adjusted accordingly and can be displayed to the patient.

The patient base station also periodically performs a capacity check on the monitor-defibrillator when the monitor-defibrillator is coupled to the patient base station during charging and maintenance operations. This is a more comprehensive check than the one performed internal to the monitor-defibrillator. The patient base station can discharge the battery fully, charge it up fully and then discharge the battery. The current that's being discharged is precise, thus, over a period of time the processor could calculate whether the actual capacity of the battery is meeting the specifications. Factors such as the amount of charge and the rate of discharge are considered.

Having the capability to perform the monitoring functions on the monitor-defibrillator rather than solely at some remote base station is beneficial because the battery is necessarily contained in the monitor-defibrillator or attached to it via an electrical connector. Thus, if the patient has traveled away from the base station, that patient would have to return to the base station to be certain that sufficient capacity remained in the battery.

Alternatively, the monitor-defibrillator could itself be designed with additional functionality to perform all of the heretofore mentioned functions of the patient base station except, preferably, for the battery recharging function. In such a system, the battery can be a "smart" battery which has an internal memory/processor that can monitor and store information regarding the status of the battery. In this system, a dedicated battery recharger, also having a processor which communicates with the memory/processor in the smart battery can be utilized which does not require the functional capability of a patient base station. The smart battery memory/processor also communicates with the monitor-defibrillator when it is connected thereto.

Furthermore, although the smart battery can have the capability to monitor and determine operational characteristics thereof, it can be desirable that the monitor-defibrillator also independently, and more precisely, monitor the condition of the smart battery, particularly, for example, during a rapid drain condition as when electrical energy is being delivered to a patient when treatment is required. It is very important for the monitor-defibrillator to very precisely monitor the battery condition to ensure that a sufficient energy supply remains in the battery. Typically, the smart battery only monitors the data storage/processor circuitry of the monitor-defibrillator and not the converter. Thus, the monitor-defibrillator uses this added information to update the memory/processor in the smart battery.

These and other objects and advantages of the invention will become apparent from the following description of certain present preferred embodiments taken in conjunction with the appended claims and the attached drawings.

DETAILED DESCRIPTION OF THE PREFERRED EMBODIMENTS

Figure 1:
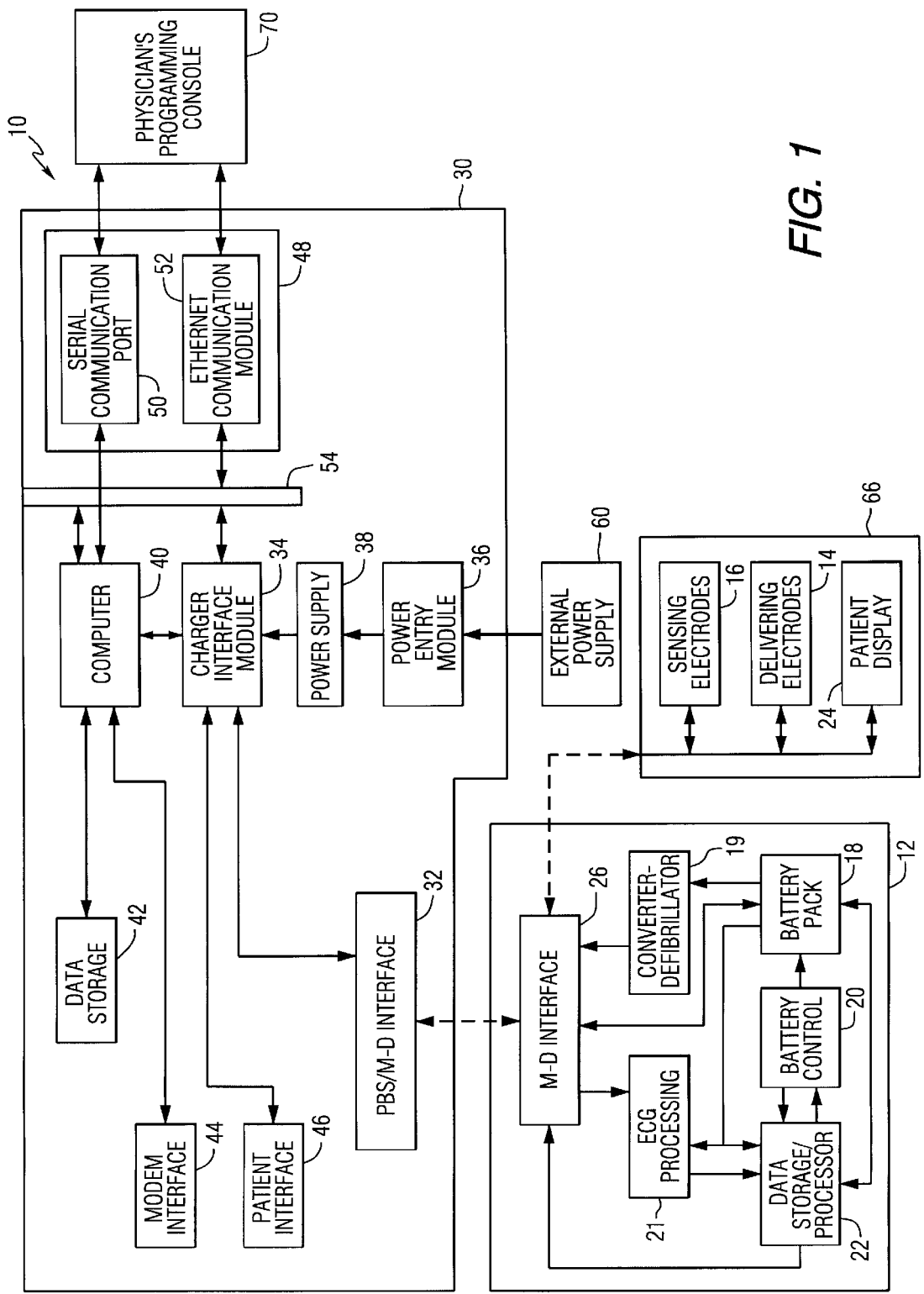
FIG. 1 is a patient base station block diagram showing the patient base station, physician's programming console and the monitor-defibrillator connected to either the patient base station or the electrode harness.

An apparatus is provided for monitoring and supporting the monitor-defibrillator electronics and the rechargeable battery pack provided therein. The system 10 of the present invention is shown schematically in FIG. 1. As can be seen from FIG. 1, the present system 10 involves a number of interrelated components. A monitor-defibrillator 12 is included which is operatively connectable via an interface module 26, to either a patient base station 30 or an electrode harness 66 having two groups of electrodes 14, 16. A group of delivering electrodes 14 is provided for delivering a cardioverting or defibrillating shock when necessary to a patient. Another group of electrodes 16 performs sensing operations in which the physiological condition of a patient may be monitored. The delivering electrodes 14 are operatively connected to a converter-defibrillator 19 located within the monitor-defibrillator 12. The electrode harness 66 also includes a patient display 24 with the capability of displaying visual messages, enunciating audio messages and activating audio alarms. The patient display 24 also includes various buttons for providing the patient with a means of input to the device. The operation of the electrode harness/ monitor-defibrillator are more particularly described in co-pending application Ser. No. 08/651,274, assigned to the present assignee and hereby incorporated by reference herein.

The battery pack 18 is responsible for providing the necessary power to operate the converter-defibrillator circuitry for delivering the cardioverting or defibrillating shock. Therefore, it is important that the energy capacity of battery 18 be ensured. The monitor-defibrillator 12 preferably utilizes a high-energy-density nickel-cadmium battery. Preferably, the battery is comprised of five 1.2 volt cells connected in series to yield six volts.

The monitor-defibrillator 12 also includes battery control circuitry 20 which can activate the battery 18 to deliver its charge to the converter-defibrillator 19 and subsequently to the delivery electrodes 14 when necessary. The battery control circuitry 20 is responsive to certain data conditions of the patient. For this reason, the battery control 20 is operatively connected to data storage/processor 22, also located within the monitor-defibrillator 12. The data storage/ processor 22 receives data from the sensing electrodes 16. The data storage/processor 22 in the monitor-defibrillator preferably utilizes non-volatile memory. The data storage/ processor 22 stores programmable system operational parameters, system operating status information, digitized ECG episodes and the results of hardware diagnostic tests. This data, through subsequent analysis, provides the means to allow reconstruction of ECG events and analysis of device performance.

The monitor-defibrillator 12 is able to perform various system and battery checks. Energy usage of the monitor-defibrillator 12 is monitored in real time to determine the useful energy remaining of the battery 18 per charge. The patient display 24 located on the electrode harness 66 indicates the operating time remaining for the battery 18. The patient may access this function at any time by pressing a button on the patient display 24. The run-time parameter is available to an external host via the communications interface located in the interface module 26. A low battery condition as determined by the monitor-defibrillator 12 is recorded in non-volatile memory of the data storage/ processor 22. The patient is also alerted to a low battery condition by the patient display 24.

The monitor-defibrillator 12 monitors the battery current consumption and, if required, makes an appropriate adjustment to the battery run-time parameter based on sampling the real-time monitor-defibrillator current consumption. The current is monitored by an analog circuit in the monitor-defibrillator 12 and is input into a comparator at a trip level of current. The voltage is monitored but is not sent to the comparator. The trip level is a level of current that is based on a precalculated worst case (i.e., maximum) average current developed for the device. For the particular hardware used with the present invention, the amount of typical maximum run current (i.e., the trip level current) is 74 milliamps. If the measured current exceeds the trip level, the comparator trips and the analog to digital converter in the data storage/processor 22 is commanded to read the analog representation of the current that is being drawn by the monitor-defibrillator 12. The monitor-defibrillator 12 measures the time period of excessive current draw and the amount of current above the trip level. Based on the measured readings, time is deducted from the battery runtime parameter by the monitor-defibrillator. The updated runtime remaining may be accessed by the patient at any time, as discussed above.

As long as the actual, measured current of the monitor-defibrillator 12 is less than the trip level current, the data storage/processor 22 presumes that the actual current is the same as the trip current when deducting time from the battery runtime parameter. Thus, although the typical maximum run current is provided as 74 mils, the battery 18 is nearly always providing a current below 74 milliamps.

The patient has the capability to access buttons on the patient display 24 that when activated will cause the remaining run time to be indicated. If a patient is very active so as to cause one of the sensing electrodes 16 to have fallen off or otherwise become disconnected from the patient, an alarm is sounded. The activation of this alarm also utilizes energy which will be subtracted from the run time.

The current measuring capability of the monitor-defibrillator 12 does not include current drawn by the converter-defibrillator 19. The monitor-defibrillator 12 tracks the periods when the converter-defibrillator 19 is actively drawing current from the battery 18 and makes adjustments to the battery run time to compensate for the energy loss.

The monitor-defibrillator 12 also makes adjustments for depletion of battery 18 capacity during periods when the device is not being used. When not in use (such as when stored on a shelf or taken by the patient on a day's outing as a spare device) the monitor-defibrillator 12 will automatically power itself up at specified intervals and make adjustments to the battery run time to compensate for energy losses due to self-discharge of the battery and current draw of monitor-defibrillator 12 components when powered down.

The monitor-defibrillator 12 will utilize measures intended to reduce depletion of battery 18 capacity in order to maximize available energy if a treatment pulse is required. The monitor-defibrillator 12 will be optimized to execute its monitoring functions as rapidly as possible and then enter a low power operating mode until the monitoring functions must again be executed. The monitor-defibrillator can be kept in a low power operating mode when not performing necessary system operating functions. Additionally, when possible, high current devices will be powered down after completing their required tasks. An example would be the analog to digital converter. By scheduling analog to digital conversion readings at the beginning of monitoring functions, the analog to digital converter can be powered down sooner than if analog to digital readings are interspersed throughout the monitoring functions.

If the run time parameter indicates that the depletion of battery 18 capacity has reached the level at which the battery 18 should be recharged utilizing the patient base station 30, then the patient display 24 will provide notification. The notification will consist of visual and/or audio indicators. The notification will require acknowledgment by the patient before it will be discontinued. The notification will be repeated at predetermined intervals, for example, every 15 minutes, until the battery 18 is recharged by the patient base station 30. The monitor-defibrillator 12 can also determine the available device operating time (prior to recharging the battery), taking into account at least: (1) adjustments for abnormally high current draw of the device including adjustments for converter operation or operation of other high current draw devices as well as adjustments for excessive current draw from a defective component; (2) adjustments for normal current draw during an elapsed time period; (3) adjustments for device fault conditions such as failure of a battery load test or a problem with operation of the converter; and (4) adjustments for depletion of battery capacity during periods of non-use. The patient display 24 or alarms can be used to notify the patient of the available device operating time.

The monitor-defibrillator 12 will also utilize an analog to digital converter located in the data storage/processor 22 to supervise the battery 18 voltage during operation of the converter-defibrillator 19. The converter-defibrillator 19 may be operated in either a fast charge mode or a slow charge mode. The fast charge mode minimizes the time to charge the converter-defibrillator 19 but at a maximized current draw from the battery 18. The slow charge mode minimizes the capacitor charging current but with an increased time to charge the converter-defibrillator 19. The converter-defibrillator 19 is normally operated in fast charge mode.

If the battery 18 voltage falls below a level at which the monitor-defibrillator 12 can reliably operate the converter-defibrillator 19, then the monitor-defibrillator 12 will switch the converter-defibrillator 19 to a slow charge mode. This will permit the battery 18 voltage level to recover to a level at which the monitor-defibrillator 12 can again reliably operate the converter-defibrillator 19. Use of the slow charge mode permits the converter to be operated and a therapy pulse delivered to the patient when the battery 18 capacity is low.

If during operation of the converter-defibrillator 19 in the slow charge mode the battery 18 voltage falls below a level at which the monitor-defibrillator 12 can reliably operate the converter-defibrillator 19, then the monitor-defibrillator 12 will deactivate the converter and evaluate the energy capability stored in the converter. If the energy stored in the converter is sufficient to deliver at least a minimal energy pulse, such as, for example, 30 joules, then the treatment cycle will continue with delivery of the available energy. If there is not enough energy stored in the converter to deliver a minimal energy pulse, then the converter will be discharged. In addition, notification will be given using the patient display 24 that the device is disabled and medical assistance should be provided to the patient.

If the monitor-defibrillator 12 determines that the battery 18 capacity has fallen below a level at which the system performance data is in danger of being corrupted then the monitor-defibrillator 12 will remove operating power. The removal of operating power will reserve the remaining battery 18 capacity for maintenance of the data storage/processor 22. The integrity of the data storage is essential to evaluating the proper operation of the device. Since this low level of battery 18 capacity is inadequate for reliable operation of the monitor-defibrillator, the best possible use of the remaining battery 18 capacity is to preserve the operational history of the device stored in the data storage/processor 22. When this state has been reached, the monitor-defibrillator will refuse to power up until connected to the patient base station 30. If required, the patient base station 30 will provide additional energy to the monitor-defibrillator 12 to insure proper functioning during this power up sequence. The patient base station will then retrieve the operational history from the monitor-defibrillator 12 and recharge the battery 18.

The analog to digital converter located in the data storage/processor 22 is powered up each interim cycle to sample the analog inputs. This interim cycle is preferably every 5 milliseconds, which generally corresponds to the ECG sampling rate. After sampling the analog inputs, the analog to digital converter is powered down to conserve battery power. There are entire portions of the monitor-defibrillator 12 that periodically go into a low current sleep mode.

Figure 4:
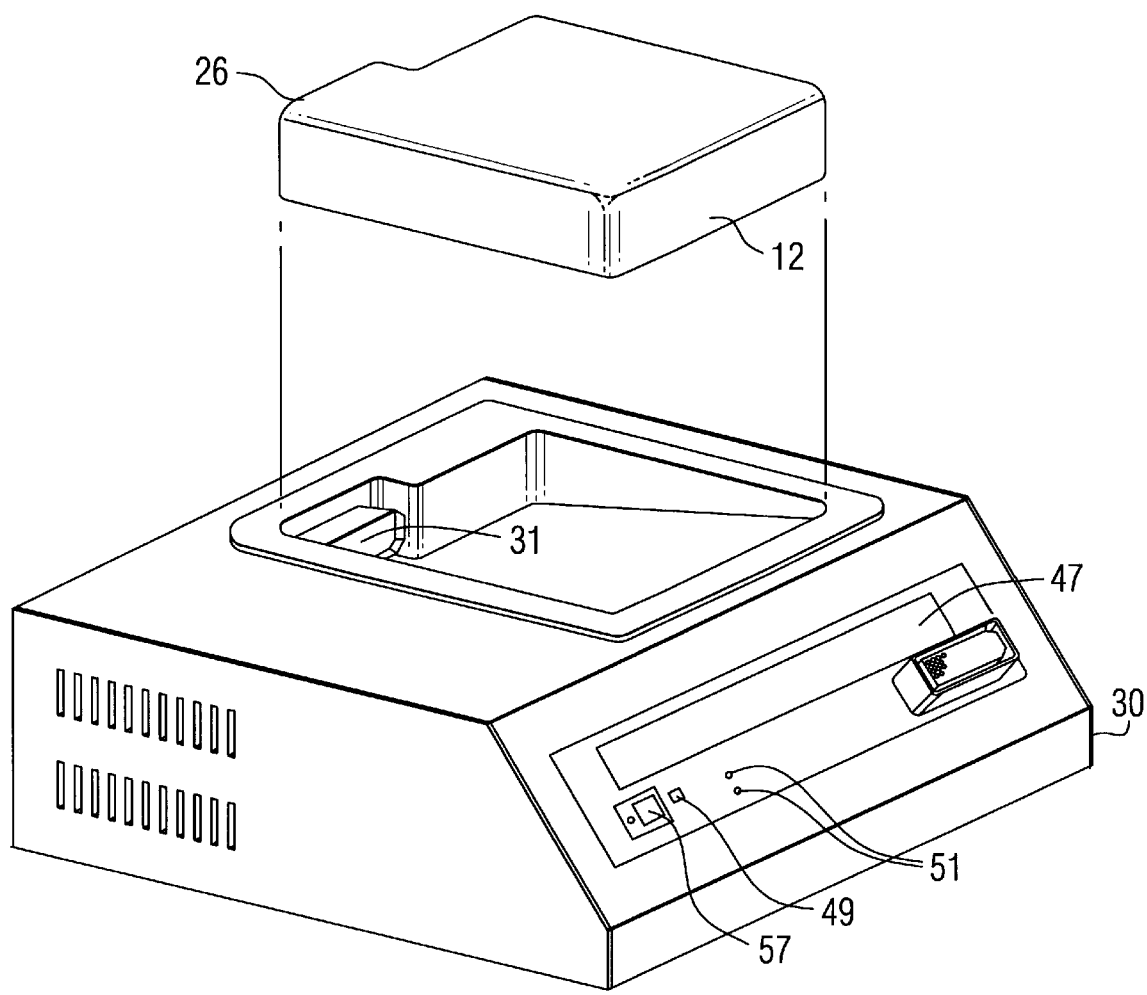
FIG. 4 is a diagrammatic perspective view of the monitor-defibrillator and patient base station.

On a routine basis the patient is required to couple the monitor-defibrillator 12 with the patient base station 30 (see FIG. 4). When the monitor-defibrillator 12 is removed from the electrode harness 66 and inserted in the receptacle 31 of the patient base station, connection is made between the monitor-defibrillator interface 26 and a monitor-defibrillator interface 32 located within the patient base station 30. The patient base station monitor-defibrillator interface 32 is thus operatively connected to the data storage/processor 22 of the monitor-defibrillator 12. In this way, the monitor-defibrillator interface 32 can download information from the memory of the data storage/processor circuitry 22; i.e., information, that was received from both the sensing electrodes 16 regarding the patient's physiological data, and also from the battery control circuitry 20 regarding the operating history of the monitor-defibrillator 12.

The monitor-defibrillator interface 32 of the patient base station 30 is also operatively connected to the battery 18. In this way, the patient base station 30 can perform comprehensive tests as to the operating parameters of the battery 18. Further, charging of the battery 18 can also be performed through the monitor-defibrillator interface 32. The battery 18 of each monitor-defibrillator 12 requires periodic charging. Thus, monitor-defibrillators 12 that are not in use are to be stored on a patient base station charging port (i.e., coupled to the monitor-defibrillator interface 32), where they undergo charging and maintenance operations. The patient base station 30 provides battery status information to the patient by way of a visual display including indicator lights as well as by audio alarms provided by the patient interface 46.

The power required to charge the battery 18 of the monitor-defibrillator 12 is supplied by either an internal or an external power supply. As shown in FIG. 1, an internal power supply 38 may be used which is operatively connected to the charger interface module 34. A switch mode type power supply 38 is preferred. However, a linear type power supply 38 could also be utilized. If a linear type power supply 38 is used, a heat sink and a fan would be needed in the patient base station 30. Use of a switch mode type power supply 38 would eliminate the fan, reduce the size of the heat sinks and would reduce the size of the system package and is thus preferred.

The power supply 38 utilizes a power entry module 36. The power entry module 36 provides a standard IEC 320 type power entry connector. The power entry module 36 functions over a full range of standard household international voltages and frequencies. The power entry module 36 shall preferably use a standard international "1/0" icon for power status indication.

The monitor-defibrillator interface 32 is operatively connected to the charger interface module 34 within the patient base station 30. The charger interface module 34 provides a standard PC-AT compatible ISA type interface and provides all the necessary bus signals for computer control of the various charger interface module functions. In this way, data received by the monitor-defibrillator interface 32 from the data storage/processor 22 of the monitor-defibrillator 12 is provided to a computer 40. In this way, communication is then established for transfer of operational data to the patient base station mass data storage area 42. This data is a record of device performance and any ECG data that may have been stored within the monitor-defibrillator 12 during patient monitoring.

Thus, the patient base station initiates data retrieval operations from the monitor-defibrillator 12 if operational or ECG data is stored within the internal memory included in the data storage/processor 22 of the monitor-defibrillator 12. As part of normal maintenance of the monitor-defibrillator 12, this data is transferred to the patient base station 30 for long-term data storage 42. The patient base station 30 may store retrieved data on a removable floppy disk, removable or fixed hard disk or other removable media. In the preferred embodiment, the data is stored on a fixed hard disk. At the successful completion of data transfer, the computer 40 of the patient base station 30 issues a clear memory command via the monitor-defibrillator interface 32 to the monitor-defibrillator 12. This command erases the temporary memory in the data storage/processor 22 in the monitor-defibrillator 12. In the embodiment utilizing rotating media, the patient base station notifies the patient when the removable media requires replacement due to inadequate storage area remaining.

The computer 40 utilized by the patient base station 30 incorporates an imbedded, PC-AT-compatible computer architecture. The computer 40 preferably utilizes an Intel™ 80×86 type central processing unit, with a performance no less than that of a 25 MHz 80386SX Intel™ processor. The computer 40 preferably includes two standard PC-AT type serial ports. A modem interface port 44 should also be available for connecting the computer 40 to a telephone modem (not shown). The modem interface 44 is designed to interface to a telephone modem with no less than 14.4 kpbs data rate capability. The modem preferably interfaces to the single board computer 40 via one of its serial ports.

A physician's programming console ("PPC") interface 48 provides a communication link from the patient base station ("PBS") 30 to a physician's programming console 70. The physician's programming console interface 48 contains an ethernet communications module 52 for providing a standard 10 Mbps data link to the physician's programming console 70. This module 52 preferably interfaces to the single board computer 40 via an expansion bus 54. Data transfers between the patient base station 30 and the physician's programming console 70 are handled via the ethernet port 52. This allows the significant amount of data generated by the monitor-defibrillator 12 to be offloaded in a reasonable time at the physician's office during the patient's periodic visits. The external panel connection for the high speed physician's programming console 70 data link can use a standard BNC type female connector. A serial communications port 50 is also part of the physician programming console interface 48 and is provided for connection of the computer 40 to the physician's programming console 70. Data transfer from the patient base station 30 to the physician's programming console 70 can also occur via high speed modem interface 44 from the patient's home.

The computer 40 is operatively connected to an ISA type expansion bus 54. The expansion bus 54 is designed to be capable of supporting up to four 16 bit expansion modules or cards. The computer 40 utilizes the expansion bus 54 to facilitate communications, control and status transfers to and from the charger interface module 34 and ethernet communication module 52 of the physicians programming console interface 48. The expansion bus 54 also provides power to the computer 40 and the ethernet communication module 52 from the charger interface module 34.

Figure 2:
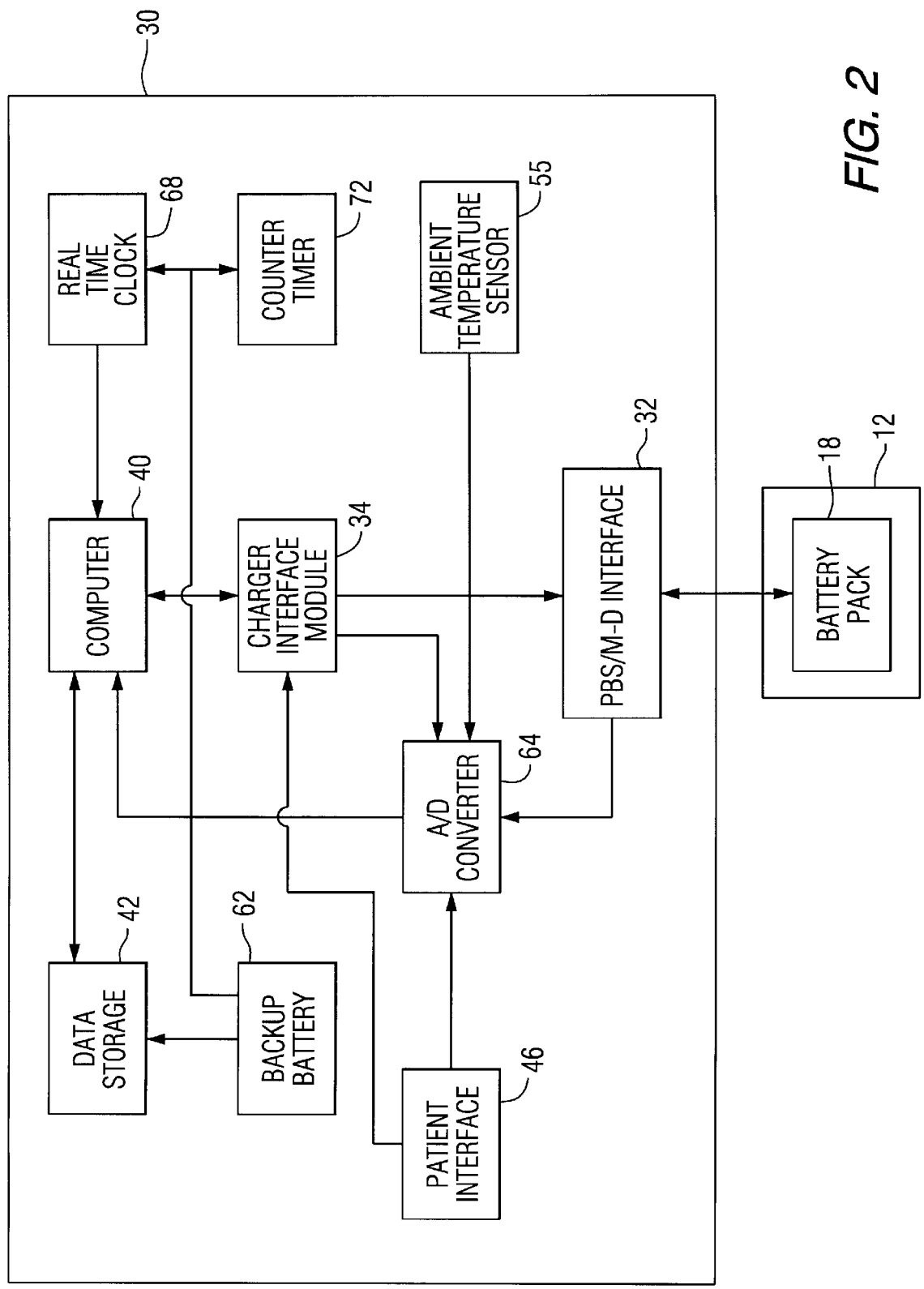
FIG. 2 is a block diagram showing the patient base station computer, real-time clock, counter timer, analog/digital converter and backup battery, and monitor-defibrillator battery connection.

The operating system and applications software for the patient base station 30 may be stored on rotating media in the mass data storage area 42. However, the preferred embodiment embeds this software in non-volatile read only memory, such as EEPROM or FLASH memory. These embodiments allow the device to operate without need of rotating media. Additional non-volatile memory is provided to store certain manufacturing information and device-specific data. These memory locations are written to only during the initial manufacturing processes and are then write inhibited by hardware means. As shown in FIG. 2, a real time clock may be implemented in conjunction with the computer 40 to maintain date and time of day information. The clock has backup power 62 provided to maintain operation if power is removed from the patient base station. A counter-timer 72 is provided to coordinate time critical operations. An analog to digital converter 64 is also provided.

The patient base station computer 40 controls battery charging, both rapid charging and float charging once the fill charge point is reached. The computer 40 also controls discharging of the battery 18, as required. A battery capacity test is periodically performed to verify the stored energy capacity of the monitor-defibrillator battery pack 18. The system processor 40 controls all battery capacity measurement operations by discharging the battery 18 to a defined starting level, rapid-charging the battery 18 to full potential, implementing a timed discharge cycle to deplete the battery 18 and calculating the actual energy capacity. This process can determine if a bad cell is present in the battery pack, or the measured battery capacity is less than a defined acceptable limit.

Figure 5:
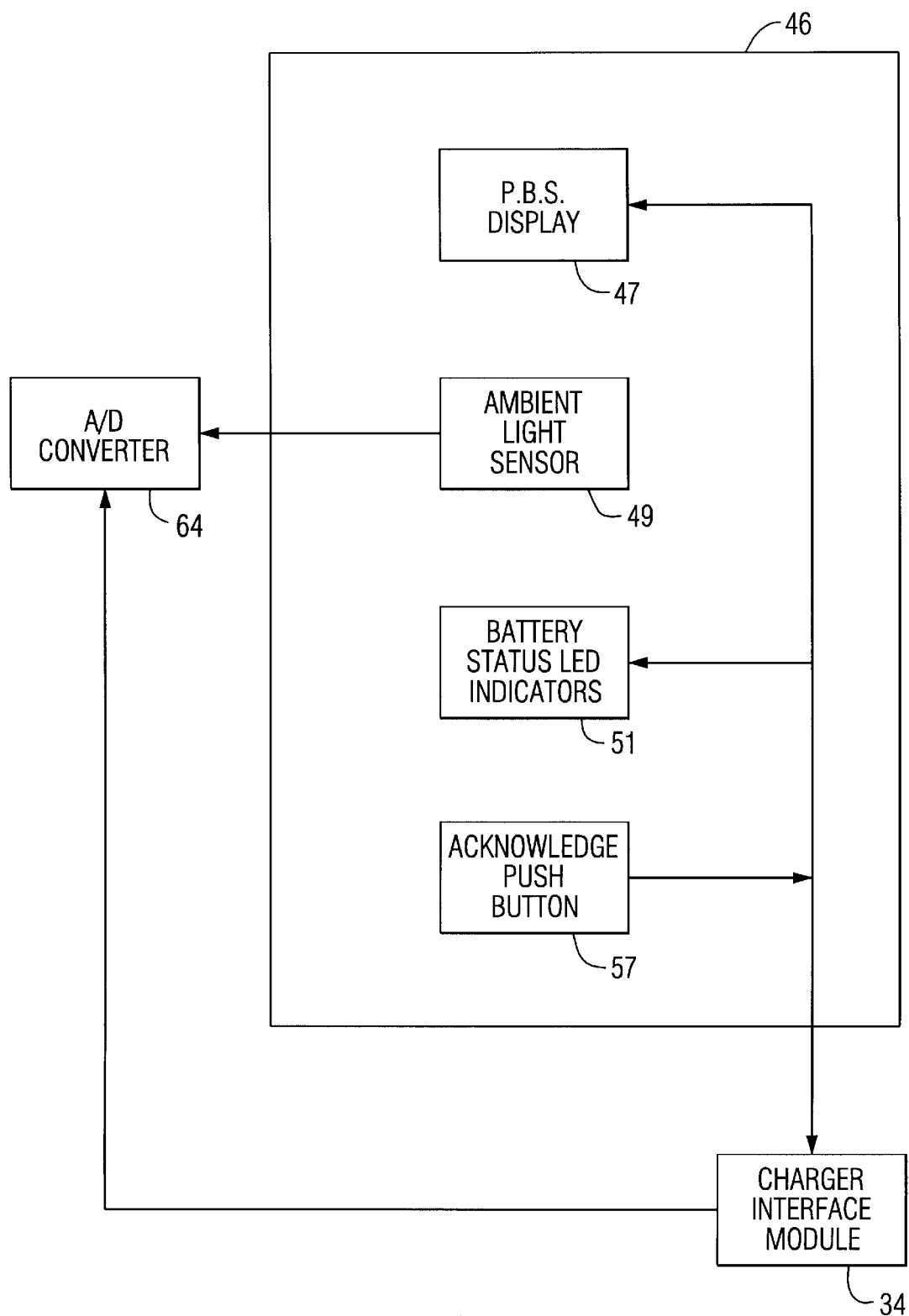
FIG. 5 is a block diagram for the patient base station patient interface module.

The patient interface module 46, as shown in FIG. 5, can have a visual display 47, battery status LED indicators 51, acknowledge push button 57 and ambient light sensor 49. The patient interface module 46 can be operatively associated with the charger interface module 34 and the analog to digital converter 64. The analog to digital converter 64 with an analog multiplexer is preferably provided within the patient base station 30. This analog to digital converter 64 allows the single board computer 40 (FIG. 1) to monitor the charging current of the charger/discharger 34, discharging current of the charger/discharger 34, the battery voltage present at the monitor-defibrillator interface 32, the ambient light sensor 49 of the patient interface module 46 and the ambient temperature within the patient base station 30 enclosure via a temperature sensor 55 (shown in FIG. 2).

Referring again to FIG. 1, the patient interface 46 in the patient base station 30 indicates the status of the monitor-defibrillator battery 18 during the battery capacity test cycle. The patient interface 46 preferably incorporates a front panel mounted vacuum fluorescent (VF) type display 47 (shown in FIG. 4). This display 47 may be a character type with standard 5 mm, 5×7 dot characters. The PBS display 47 is preferably arranged in one of the following configurations: a 2 line by 40 character or a 4 line by 20 character. The PBS display 47 is controlled by the single board computer 40 via the charger interface module 34 through a parallel data interface. As an alternative, a graphics type LCD may be used for the PBS display 47. If an LCD display is used, the patient base station may include an ambient light sensor 49 to control the LCD backlight for improved readability.

In addition, the patient base station 30 tracks battery 18 usage and notifies the patient when replacement of the battery 18 is required. If the battery 18 expiration parameters have been exceeded (the expiration date or the number of charge cycles), the battery 18 can still be used by the monitor-defibrillator 12, but the patient will be notified to replace the monitor-defibrillator 12 as soon as possible. The number of charging cycles performed on the battery 18 is recorded in the monitor-defibrillator memory of the data storage/processor 22. Also, the date the battery 18 was installed in the monitor-defibrillator 12, the type of cell used in the battery 18, and the expiration date of the battery 18 as well as any other pertinent information is stored in monitor-defibrillator data storage/processor 22.

The communications interface created when the patient base station 30 and attached monitor-defibrillator 12 is connected to the physician's programming console 70 is utilized during the initial configuration programming of the monitor-defibrillator 12. Preferably, the following information is configured: name, address, telephone number, hospital, attending physician, medications; monitor-defibrillator detection and treatment parameters such as heart rate threshold or rate cutoff, defibrillation energy to be delivered in therapy pulses; and monitor-defibrillator manufacturing data such as device serial numbers, monitor-defibrillator battery pack. and expiration date, electrode harness(es) and expiration date(s).

A data communications protocol facilitates the transfer of digital information between the patient base station 30 and the physician's programming console 70. This protocol consists of transferring data in blocks or frames. To ensure the integrity of transmitted and received data, the protocol implements error checking techniques.

The patient base station 30 to physician's programming console 70 communications protocol consists of transferring data in frames. Communication frames are transferred via the serial communication port 50. Serial communication port 50 hardware control lines are utilized to provide hand-shaking between the patient base station 30 and the physician's programming console 70 that will delimit the frame boundaries. Each communication cycle consists of a command frame sent from the physician's programming console 70 to the patient base station 30, followed by a response frame sent from the patient base station 30 to the physician's programming console 70. Each command frame will contain a command code followed by any relevant data, followed by an error checking code such as a CRC code.

If the command is successfully processed by the patient base station 30, the patient base station 30 will return a response frame that contains an ACK code, followed by the original received command code, followed by any relevant data, followed by an error checking code such as a CRC code.

If the command is not successfully processed by the patient base station 30, the patient base station 30 will return a response frame that contains a NAK code, followed by the original received command code, followed by any relevant data, followed by an error checking code such as a CRC code.

If a command frame is received by the patient base station 30 that contains an invalid error checking code, the patient base station 30 will ignore the communication frame. The physician's programming console 70 will be responsible for monitoring the patient base station 30 response. If the patient base station 30 does not respond to a command frame the physician's programming console 70 can elect to resend the frame.

If a response frame is received by the physician's programming console 70 that contains an invalid error checking code, the physician's programming console 70 can elect to resend the frame.

Another data communications protocol facilitates the transfer of digital information between the monitor-defibrillator 12 and the patient base station 30. The protocol consists of transferring data in blocks or frames.

The patient base station ("PBS") 30 to monitor-defibrillator ("M-D") 12 communications protocol consists of transferring data in frames. Communication frames are transferred via the PBS/M-D interface 32. PBS/M-D interface 32 hardware control lines are utilized to provide handshaking between the patient base station 30 and the monitor-defibrillator 12 that will delimit communication frame boundaries. Each communication cycle consists of a command frame sent from the patient base station 30 to the monitor-defibrillator 12, followed by a response frame sent from the monitor-defibrillator 12 to the patient base station 30. Each command frame will contain a command code followed by any relevant data, followed by an error checking code such as a CRC code.

If the command is successfully processed by the monitor-defibrillator 12, the monitor-defibrillator 12 will return a response frame that contains an ACK code, followed by the original received command code, followed by any relevant data, followed by an error checking code such as a CRC code.

If the command is not successfully processed by the monitor-defibrillator 12, the monitor-defibrillator 12 will return a response frame that contains a NAK code, followed by the original received command code, followed by any relevant data, followed by an error checking code such as a CRC code. The patient base station 30 will determine and execute a response appropriate for the failed monitor-defibrillator 12 command process.

If a command frame is received by the monitor-defibrillator 12 that contains an invalid error checking code, the monitor-defibrillator 12 will return a response frame that contains a code indicating that the command was not properly received and should be resent. The patient base station 30 can elect to resend the command frame.

If a response frame is received by the patient base station 30 that contains an invalid error checking code, the patient base station 30 can elect to resend the frame or initiate monitor-defibrillator 12 fault condition processing.

The patient base station 30 offers a collection of commands that the physician's programming console 70 can utilize during communications with the patient base station 30. The command set provides a means to initiate various patient base station 30 and monitor-defibrillator 12 diagnostic, configuration, and data retrieval procedures.

The physician's programming console 70 can gain access to various monitor-defibrillator 12 information and operational features by issuing commands to the patient base station 30 via the serial communications port 50. Upon receipt of these commands, the patient base station 30 will issue the appropriate commands to the monitor-defibrillator 12 via the PBS/ M-D interface 32, that will carry out the desired operation. The patient base station 30 will return to the physician's programming console 70 the monitor-defibrillator 12 response to the operation.

A digital output from the monitor-defibrillator data storage/processor is provided to control the activation of the battery test load. Activation of the load places a high current demand on the monitor-defibrillator battery 18. This determines if the monitor-defibrillator battery pack contains any defective cells. The monitor-defibrillator 12 can determine the available device operation time (prior to recharging the battery) utilizing adjustments for abnormally high current draw, normal current draw, device fault conditions, and depletion of battery capacity during periods when the device is not in use.

Upon command from the patient base station or the monitor-defibrillator display, the monitor-defibrillator 12 performs a battery load test. The monitor-defibrillator 12 returns a pass-fail indication to the patient base station or the display. Load tests are most often performed with the display as the host. If the battery 18 fails the load test, the battery voltage measurement prior to the load test and at the point of failure are stored in the monitor-defibrillator non-volatile memory.

Figure 3:
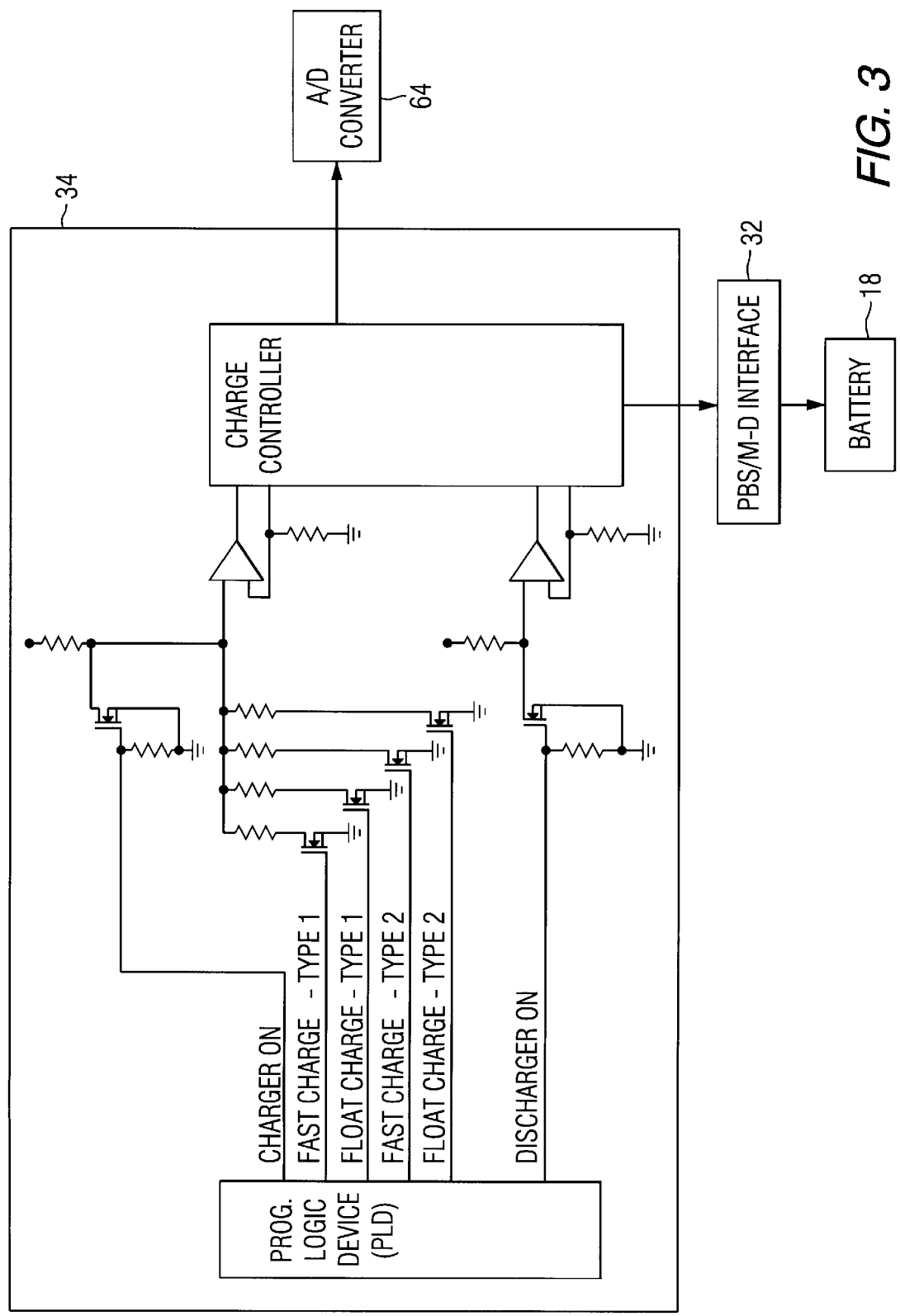
FIG. 3 is a block diagram for the battery load test function.

Referring to FIG. 3, the patient base station 30 provides circuitry in the charger interface module 34, that can charge or discharge the monitor-defibrillator 12 battery pack 18. The charger interface module 34 connects to the monitor-defibrillator 12 battery pack 18 via the PBS/M-D interface 32. Prior to battery pack 18 maintenance operations, the patient base station 30 will retrieve battery pack 18 identification information from the monitor-defibrillator 12 via the PBS/M-D interface 32.

Two charging modes are provided; rapid charging and float charging. During the rapid charge cycle the charger interface module 34 supplies charging current at the one hour charge rate of the battery pack 18. During float charge operations, the charger interface module 34 supplies charging current at the continuous maintenance rate of the battery pack 18.

The rapid and float charge current rates supplied by the charger interface module 34 are adjustable by the patient base station computer 40. The patient base station computer 40 will configure the charger interface module 34 to supply a charge current rate that is appropriate for the connected battery pack 18.

During the discharge cycle, the charger interface module 34 provides a resistive load to the battery pack 18 that discharges the battery pack 18 at the one hour discharge rate of the battery pack 18. The discharge resistive load applied by the charger interface module 34 is adjustable by the patient base station computer 40. The patient base station computer 40 will configure the charger interface module 34 to apply a resistive load that causes a one hour current drain rate that is appropriate for the connected battery pack 18.

The battery charger interface module 34 can be controlled by the patient base station computer 40 or by the monitor-defibrillator 12 via the PBS/M-D interface 32. Monitor-defibrillator 12 control of the charger interface module 34 is accomplished by activating I/O control lines located in the PBS/M-D interface 32. These I/O lines will configure the charger interface module 34 for the desired charge/discharge operation. Alternately, the patient base station computer 40 can control the I/O lines and configure the charger interface module 34 for the desired charge/discharge operation. Under normal operation the monitor-defibrillator 12 controls the configuration of the charger interface module 34. The patient base station 30 configuration of the charger interface module 34 is a redundant feature that can be utilized if certain monitor-defibrillator 12 fault conditions exist such as a totally discharged monitor-defibrillator 12 battery pack 18.

Battery pack 18 charge and discharge cycles are initiated by the patient base station computer 40. When a monitor-defibrillator 12 is connected to the patient base station 30, the patient base station 30 retrieves monitor-defibrillator 12 battery operational status data from the data storage/processor 22 via PBS/M-D interface 32. The retrieved battery operational status data includes information such as the remaining battery capacity, fault condition flags, expiration parameters, battery maintenance parameters, and battery identification information. The patient base station 30 analyzes the retrieved battery data to determine the appropriate battery pack 18 maintenance procedure.

If the patient base station 30 determines that a rapid charge cycle is required, a command to initiate a rapid charge cycle will be sent to the monitor-defibrillator 12 via the PBS/M-D interface 32. Upon receipt of this command, the monitor-defibrillator 12 will configure the charger interface module 34 for rapid charge operation by activating I/O control lines located in the PBS/M-D interface 32. The monitor-defibrillator 12 will monitor the rapid charge sequence for completion and fault conditions. Successful rapid charge completion is determined by the monitor-defibrillator 12 monitoring the voltage level at the battery pack 18 positive terminal via the A/D converter located in the data storage/processor module 22. Successful rapid charge completion can also be declared if the monitor-defibrillator 12 detects a defined change in battery pack 18 temperature. The monitor-defibrillator 12 monitors the battery temperature via a temperature sensor located in the battery pack 18 and the A/D converter located in the data storage/processor module 22. When the monitor-defibrillator 12 detects a successful rapid charge completion, the monitor-defibrillator 12 will configure the charger interface module 34 for float charge operation by activating I/O control lines located in the PBS/M-D interface 32, reset the monitor-defibrillator 12 runtime parameter to the maximum value, and issue a rapid charge complete communications frame to the patient base station 30 via the PBS/M-D interface 32.

The rapid charge cycle will be aborted if the monitor-defibrillator 12 detects one of the following conditions: a battery pack 18 over voltage condition; a battery pack 18 over temperature condition; or a defined time interval elapsed without a rapid charge completion detected. The limit values are manufacturing parameters that are stored in the monitor-defibrillator 12 data storage/processor module 22.

If the monitor-defibrillator 18 aborts the rapid charge cycle the following operations will be performed: the monitor-defibrillator 12 will configure the charger interface module 34 for float charge operation by activating I/O control lines located in the PBS/M-D interface 32; the monitor-defibrillator 12 will set it's runtime parameter to zero, which will cause patient warning messages on the display 24; and the monitor-defibrillator 12 will issue a rapid charge fault communications frame to the patient base station 30 via the PBS/M-D interface 32. If the patient base station 30 receives a rapid charge fault communications frame from the monitor-defibrillator 12, the following operations will be performed: the event will be logged in the patient base station 30 operations log file located in the data storage module 42; and the patient base station 30 will activate a patient warning message that indicates the monitor-defibrillator 12 should be serviced.

During the rapid charge cycle, the patient base station 30 will insure proper charge operation by monitoring various system parameters. The system parameter limit values are stored in the data storage module 42 during the patient base station 30 manufacturing process.

The charging current supplied to the battery pack 18 is monitored for proper levels via an A/D converter 64 (FIG. 5) channel connected to the charger interface module 34. If the measured current is outside the defined limits, the patient base station 30 will abort the rapid charge cycle.

The charging voltage on the battery pack 18 is monitored for proper levels via an A/D converter 64 channel connected to the charger interface module 34. If the measured voltage is outside the defined limits, the patient base station 30 will abort the rapid charge cycle.

The patient base station 30 will abort the rapid charge cycle if the counter timer 72 (FIG. 2) indicates the charge cycle exceeded the maximum charge completion interval.

If the patient base station 30 determines that a rapid charge cycle abort is required, the following operations will be performed: an abort rapid charge cycle command will be issued to the monitor-defibrillator 12 via the PBS/M-D interface 32; the patient base station 30 will configure the charger interface module 34 for float charge operation; the patient base station 30 will issue a command to the monitor-defibrillator 12 to set the runtime parameter to zero, which will cause patient warning messages on the display 24; the event will be logged in the patient base station 30 operations log file located in the data storage module 42; and the patient base station 30 will activate a patient warning message that indicates the monitor-defibrillator 12 should be serviced.

The patient base station 30 may initiate a discharge cycle of the monitor-defibrillator 12 battery pack 18. The discharge cycle is utilized both during the battery capacity test as well as during the process of reconditioning the battery energy storage capabilities.

If the patient base station 30 determines that a discharge cycle is required, a command to initiate a discharge cycle will be sent to the monitor-defibrillator 12 via the PBS/M-D interface 32. Upon receipt of this command the monitor-defibrillator 12 will set the monitor-defibrillator 12 runtime parameter to zero and configure the charger interface module 34 for discharge operation by activating I/O control lines located in the PBS/M-D interface 32. The monitor-defibrillator 12 will monitor the discharge sequence for completion and fault conditions. Successful discharge completion is determined by the monitor-defibrillator 12 detecting the defined final discharge voltage threshold on the battery pack 18 positive terminal via the A/D converter located in the data storage/processor module 22. When the monitor-defibrillator 12 detects a successful discharge completion, the monitor-defibrillator 12 will configure the charger interface module 34 for float charge operation, by activating I/O control lines located in the PBS/M-D interface 32, and issue a discharge complete communications frame to the patient base station 30 via the PBS/M-D interface 32.

The discharge cycle will be aborted if the monitor-defibrillator 12 detects one of the following conditions: a battery pack 18 over temperature condition; or a defined time interval has elapsed without the detection of the discharge complete condition. The limit values are manufacturing parameters that are stored in the monitor-defibrillator 12 data storage/processor module 22.

If the monitor-defibrillator 12 aborts the discharge cycle the following operations will be performed: the monitor-defibrillator 12 will configure the charger interface module 34 for float charge operation by activating I/O control lines located in the PBS/M-D interface 32; and the monitor-defibrillator 12 will issue a discharge fault communications frame to the patient base station 30 via the PBS/M-D interface 32. If the patient base station 30 receives a discharge fault communications frame from the monitor-defibrillator 12, the event will be logged in the patient base station 30 operations log file located in the data storage module 42 and a patient warning message will be activated on the PBS display 47 that indicates the monitor-defibrillator 12 should be serviced.

During the discharge cycle, the patient base station 30 will insure proper discharge operation by monitoring various system parameters. The system parameter values are stored in the data storage module 42 during the patient base station 30 manufacturing process.

The discharge current drawn from the battery pack 18 is monitored for proper levels via an A/D converter 64 channel connected to the charger interface module 34. If the measured current is outside the defined limits, the patient base station 30 will abort the discharge cycle.

The discharge voltage on the battery pack 18 is monitored for proper levels via an A/D converter 64 channel connected to the charger interface module 34. If the measured voltage is outside the defined limits, the patient base station 30 will abort the discharge cycle.

The patient base station 30 will abort the discharge cycle if the counter timer 72 indicates the discharge cycle exceeded the maximum discharge completion interval.

If the patient base station 30 determines that a discharge cycle must be terminated, the following operations will be performed: an abort discharge cycle command will be issued to the monitor-defibrillator 12 via the PBS/M-D interface 32; the patient base station 30 will configure the charger interface module 34 for float charge operation; the patient base station 30 will issue a command to the monitor-defibrillator 12 to set the runtime parameter to zero, which will cause patient warning messages on the display 24; the event will be logged in the patient base station 30 operations log file located in the data storage module 42; and the patient base station 30 will activate a patient warning message that indicates the monitor-defibrillator 12 should be serviced.

The rapid charge cycle or discharge cycle will not be initiated if the monitor-defibrillator 12 determines that the battery pack 18 temperature is outside a set of defined limits. The limit values are manufacturing parameters that are stored i n the monitor-defibrillator 12 data storage/processor module 22.

If the monitor-defibrillator 12 is removed from the patient base station 30 prior to completion of all battery pack maintenance operations, a message and alarm will be activated on the patient interface module 46. The message will indicate the monitor-defibrillator maintenance is not complete and to return the monitor-defibrillator to the patient base station. The interrupted maintenance procedure will be continued if the removed monitor-defibrillator 12 is reconnected to the patient base station 30.

The energy delivery capabilities of the battery pack 18 are periodically verified by testing the battery 18 energy capacity and high current delivery capabilities. The patient base station 30 will perform an energy capacity test on the battery pack 18 if the elapsed time from the last capacity test, as indicated by data retrieved from monitor-defibrillator data storage/processor module 22 via the PBS/M-D interface 32, exceeds the maximum time interval parameter stored in the data storage module 42, or status data retrieved from monitor-defibrillator data storage/processor module 22 via the PBS/M-D interface 32, indicates that the battery 18 operational performance was deficient during the previous patient monitoring cycle.

The battery 18 energy capacity test procedure consists of the following operations: the patient base station 30 will activate a message on the patient interface 46 visual display 47 that indicates the monitor-defibrillator 12 is being tested and to wait for the test to complete; the patient base station 30 initiates a battery discharge cycle to condition the battery for a full charge cycle; initiate a rapid charge cycle when the discharge cycle is complete to charge the battery 18 to full capacity; the patient base station 30 initiates a second discharge cycle when the rapid charge cycle is complete; and the patient base station 30 initiates a final rapid charge cycle at the completion of the second discharge cycle to ready the battery 18 for service. The duration of the second discharge cycle is timed by a counter timer located in the monitor-defibrillator 12 data storage/processor module 22. At the completion of the second discharge cycle the monitor-defibrillator 12 will compare the measured battery 18 discharge time with an acceptance parameter stored in storage/processor module 22. If the capacity discharge time is within the acceptable limit, monitor-defibrillator 12 will issue a capacity discharge pass communications frame to the patient base station 30 via the PBS/M-D interface 32.

If the capacity discharge time is not within the acceptable limit, the monitor-defibrillator 12 will set a battery capacity fault status flag located in the data storage/processor module 22, and issue a capacity discharge fault communications frame to the patient base station 30 via the PBS/M-D interface 32. The patient base station 30 will log the event in a log file located in the data storage module 42. Whenever the patient base station 30 receives a capacity discharge fault indication from the monitor-defibrillator 12, a patient warning message will be activated which indicates that the monitor-defibrillator 12 should be serviced as soon as possible. Each time a monitor-defibrillator 12 is connected to the patient base station 30, the patient base station 30 will retrieve the monitor-defibrillator 12 battery capacity fault status flag located in the data storage/processor module 22. If the battery capacity fault status flag is active, the patient base station 30 will initiate normal battery maintenance operations, with the exception of the battery capacity test which will no longer be performed. The patient base station 30 will also issue a command to the monitor-defibrillator 12 to set the runtime parameter to zero. This will cause repeated patient warning messages on the patient display 24.

If the battery status information indicates that the expiration date of the battery 18 has been exceeded (status information is entered during the initial configuration programming) or if the maximum number of charge cycles has been exceeded, the patient will be notified by the patient base station 30 that the monitor-defibrillator 12 should be serviced. The notification sequence will be activated until the patient acknowledges receipt by pressing a button 57 (FIG. 4) on the patient interface 46, or the monitor-defibrillator 12 is removed from the patient base station 30. Normal battery maintenance will continue so that the patient may use the monitor-defibrillator 12.

When a rapid charge cycle or battery discharge cycle is initiated, the patient base station 30 will deactivate the particular one of the battery status LED indicators 51 which is the "READY" LED indicator on the patient interface module 46 and activate the particular one of the battery status LED indicators 51 which is the "CHARGING" LED indicator. During the rapid charge cycle, the patient base station 30 displays a message on the patient interface visual display 47 that the monitor-defibrillator battery 18 is being charged and the monitor-defibrillator 12 is not ready for use.

If monitor-defibrillator maintenance operations are complete at the conclusion of a successful rapid charge cycle, the patient base station performs the following:

A message is displayed on the PBS display 47 indicating that the monitor-defibrillator 12 is ready for use; the PBS 30 "READY" LED 51 is activated; the "CHARGING" LED 51 is deactivated; and the monitor-defibrillator 12 is powered down.

The patient base station 30 logs the following battery maintenance information into a maintenance log: the start and completion times of battery operations; the length of the charge/discharge cycles; any abnormal conditions; and the charge cycle count, and if enabled, the battery voltage measurements taken during charge and discharge cycles. The maintenance log is stored in the data storage module 42.

The patient base station 30 issues various diagnostic test commands to the monitor-defibrillator 12. These tests are performed on a regular basis. Some tests are performed each time the monitor-defibrillator 12 is connected to the patient base station 30. Others are performed only as required. The monitor-defibrillator 12 executes the received commands and reports the test results to the patient base station 30. The patient base station 30 maintains a log of the test results on the mass storage media 42. If a fault is detected during any diagnostic procedure, the patient is notified of the condition along with the appropriate corrective action.

Other variations are also possible. For example, the preferred patient base station 30 utilizes a charger interface module board. Stacked on top of that board are purchased assemblies of PC104 boards which form the CPU module 40 and Ethernet module 52. These boards are ISA compatible because the expansion bus 54 is an ISA type bus. The stacks of PC104 boards require a great deal of cabling which is very costly. Thus, all of the major system functions could be implemented on a single PC board. This would eliminate much of the cabling.

Figure 6:
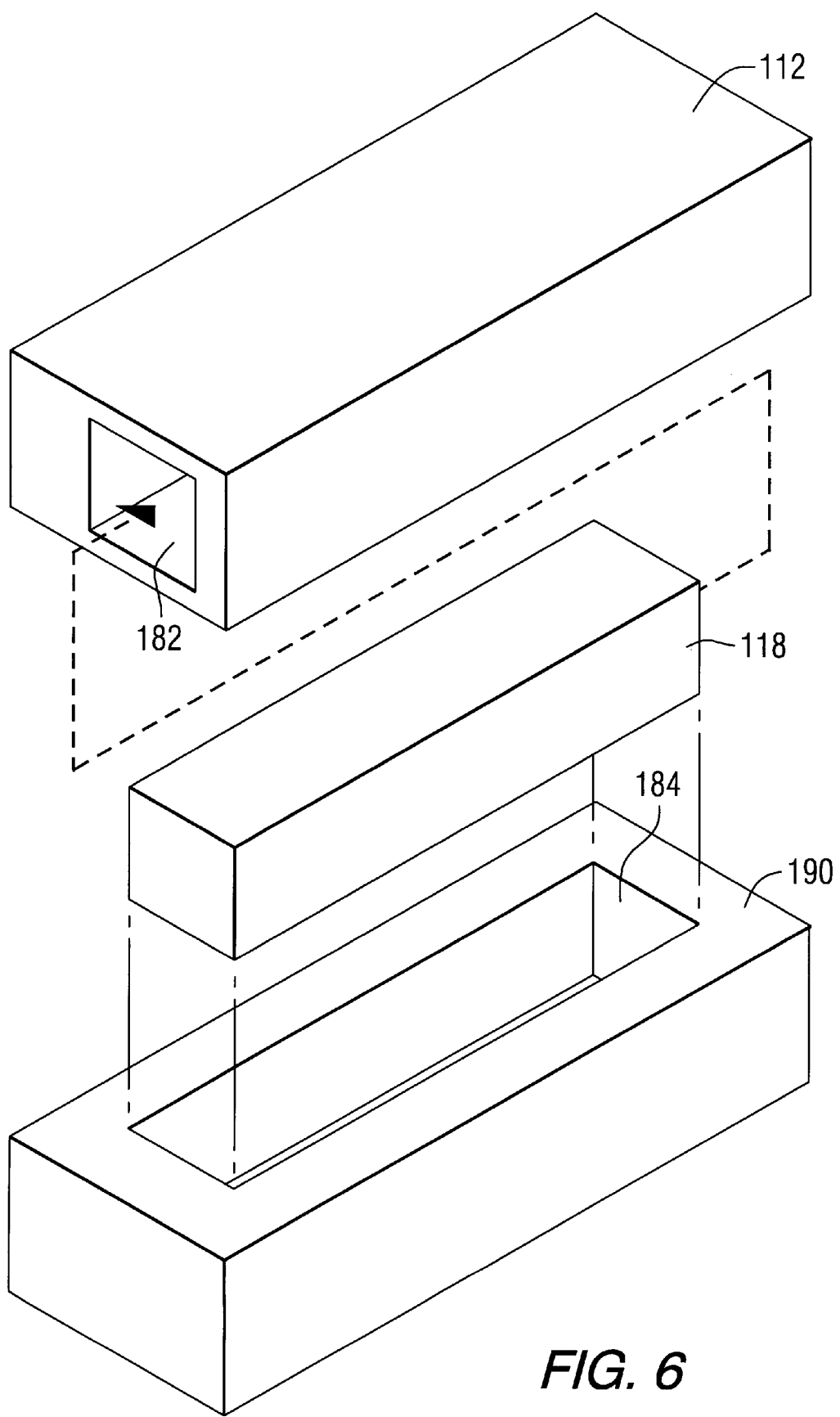
FIG. 6 is a simplified diagrammatic perspective view of an alternative embodiment of a monitor defibrillator, battery pack and battery recharger.

Moreover, alternative embodiments of the battery management system are contemplated. Particularly, referring to FIG. 6, a basic perspective view of an alternative embodiment of a battery management system 110 is shown having a monitor defibrillator 112, rechargeable battery pack 118 and battery pack recharger 190. A battery pack receptacle 182 is provided in the monitor-defibrillator 112 wherein the battery pack 118 is adapted to be received for use as a power supply. Also, the recharger 190 includes a battery pack receptacle 184 to receive the battery pack 118 for recharging and, if desired, testing to determine the operational condition of the battery pack 118. The battery pack 118 memory/processor is configured to exchange information with both a processor in the recharger 190 and the data storage/processor 22 in the monitor-defibrillator 112.

Figure 7:
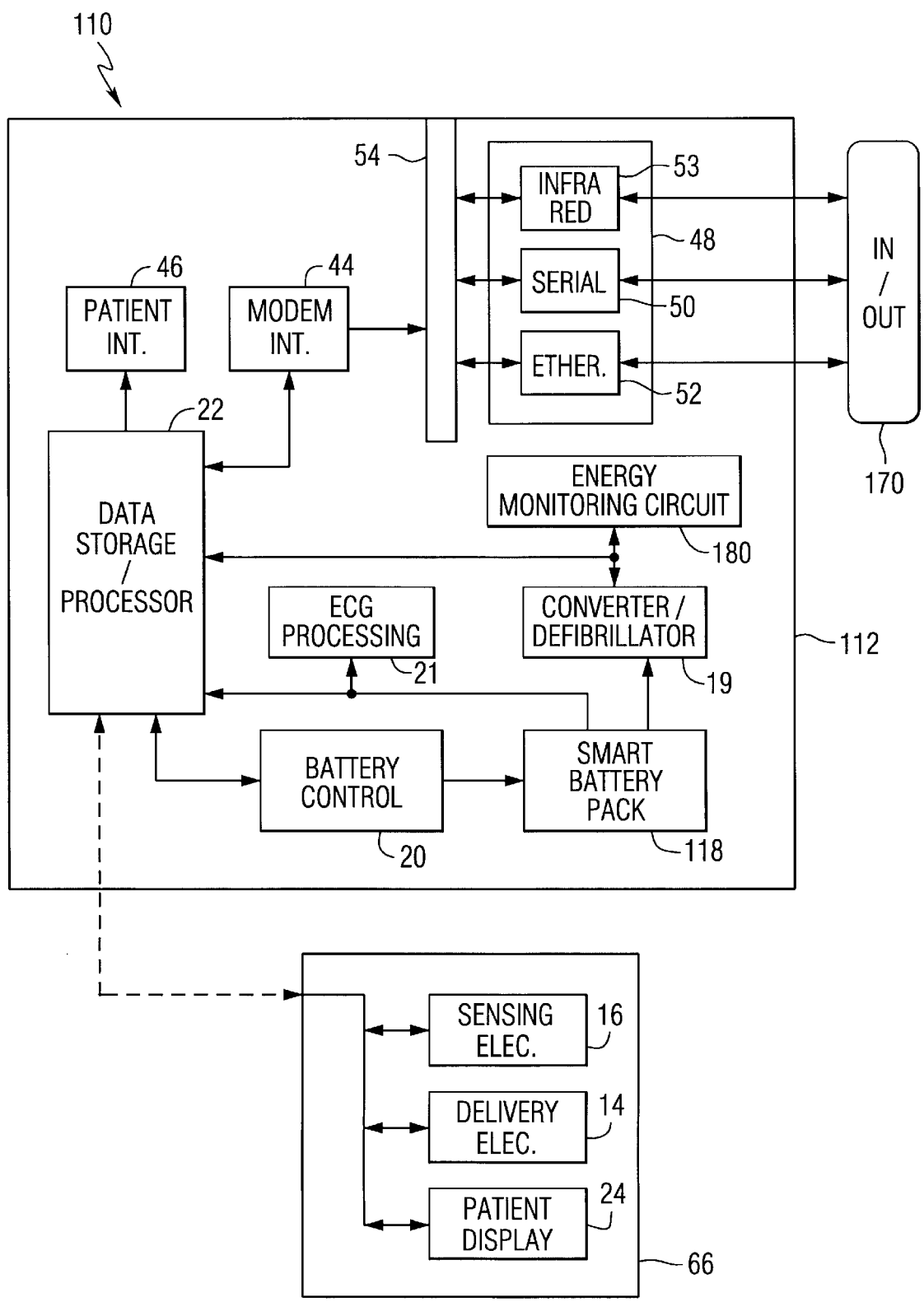
FIG. 7 is a simplified diagram illustrating a presently preferred alternative embodiment of a monitor-defibrillator.

As can be seen in the simplified diagram shown in FIG. 7, all of the heretofore described functions carried out by the patient base station 30, except for the battery recharging and related functions, can be carried out by an upgraded monitor-defibrillator 112 having increased functional capabilities. Basically, the monitor-defibrillator 112 package has been upgraded/expanded to include the circuitry necessary to perform the functions of not only the previously described monitor-defibrillator 12, but additionally, the functions formerly performed by the patient base station 30. Of course, some of the components in the previous embodiments of the monitor-defibrillator 12 and patient base station 30, are eliminated, for example the respective interface modules 26 and 32, external power supply 60, power entry module 36, power supply 38, computer 40 and battery charger interface module 34 that are not required for the expanded function monitor-defibrillator 112. Some of the components are obsoleted by the fact that the monitor-defibrillator 112 no longer interfaces with a base station. Other components, such as those related to battery recharging will be part of the battery charger 190 to be used with the smart battery pack 118. Thus, the monitor-defibrillator 112 can include maintenance circuitry for providing an indication of the operation condition of the monitor-defibrillator 112 whereas the battery recharger 190 can include battery maintenance circuitry for providing an indication of the operating condition of the rechargeable battery pack 118.

Other elements of the prior embodiment of the battery management system 10, such as the computer 40, are redundant with components in the monitor-defibrillator 112. For example, the data storage/processor 22 is also a "computer." However, the functioning of the data storage/processor 22 may also be upgraded with regard to memory and processing capabilities in order to handle the added functionality taken over by the monitor-defibrillator 112. Additionally, another input/output 170 option is an infrared communication module 53, which can be used in addition to the serial port 50 or ethernet module 52.

The battery management system 110 also contemplates the use of what is known as a "smart battery" pack 118. A smart battery is a relatively new type of battery which has an internal memory/processor that monitors the condition of the battery and can also communicate with a battery recharger 190 designed to recharge such smart battery packs. The pack recharger 190 also has a processor to read and update the memory/processor in the smart battery pack 118. Moreover, the recharger 190 can include the battery pack recharging, maintenance and testing functionality previously performed by the patient base station 30. Additionally, the smart battery pack 118 memory/processor can communicate with data storage/processor 22 in the monitor-defibrillator 112. A preferred smart battery pack 118 and recharger 190 are described in more detail below, in connection with FIGS. 8 and 9.

As explained above, the monitor-defibrillator 112 performs, in addition to the functions previously described for the monitor-defibrillator 12, all the functions previously associated with the patient base station 30, except battery recharging. The monitor-defibrillator 112 has a receptacle 182 adapted to receive the smart battery pack 118 for use as a power supply, communicates therewith to ascertain the battery condition stored in the memory of the smart battery 118, performs test operations thereon, and can update the internal memory regarding the battery condition when appropriate. Both the battery pack 118 and the battery pack receptacle 182 in the monitor-defibrillator 112 are provided with the requisite contacts and interfaces necessary for the monitor-defibrillator to be powered by the battery pack 118 and also for the data storage/processor 22 in the monitor-defibrillator 112 to exchange information with the memory/processor in the smart battery pack 118.

As will be described below in more detail, the smart battery pack 118 is equipped to monitor the battery drain only for the computer circuitry of the monitor-defibrillator 112, it is not designed to monitor the current drain caused by the high voltage converter. Thus, the upgraded monitor-defibrillator 112 can independently monitor the charge status of the battery. This separate energy monitoring function can be, for example, provided by an "energy monitoring circuit" 180 which very precisely measures the energy output of the converter-defibrillator circuit 19, which energy is, of course, provided by the smart battery pack 118. The monitor-defibrillator 112 can then update the memory of the smart battery pack 118 with this information to determine the final condition of the battery regarding the available energy.

The smart battery and recharger hardware will supply various diagnostic capabilities to the battery management system. The capabilities will include providing accurate run-time information to the monitor-defibrillator 112, storage of fault flag information for both the monitor-defibrillator 112, and storage of information which allows both the battery charger and monitor-defibrillator 112 to adapt operation to different types of smart batteries.

Figure 8:
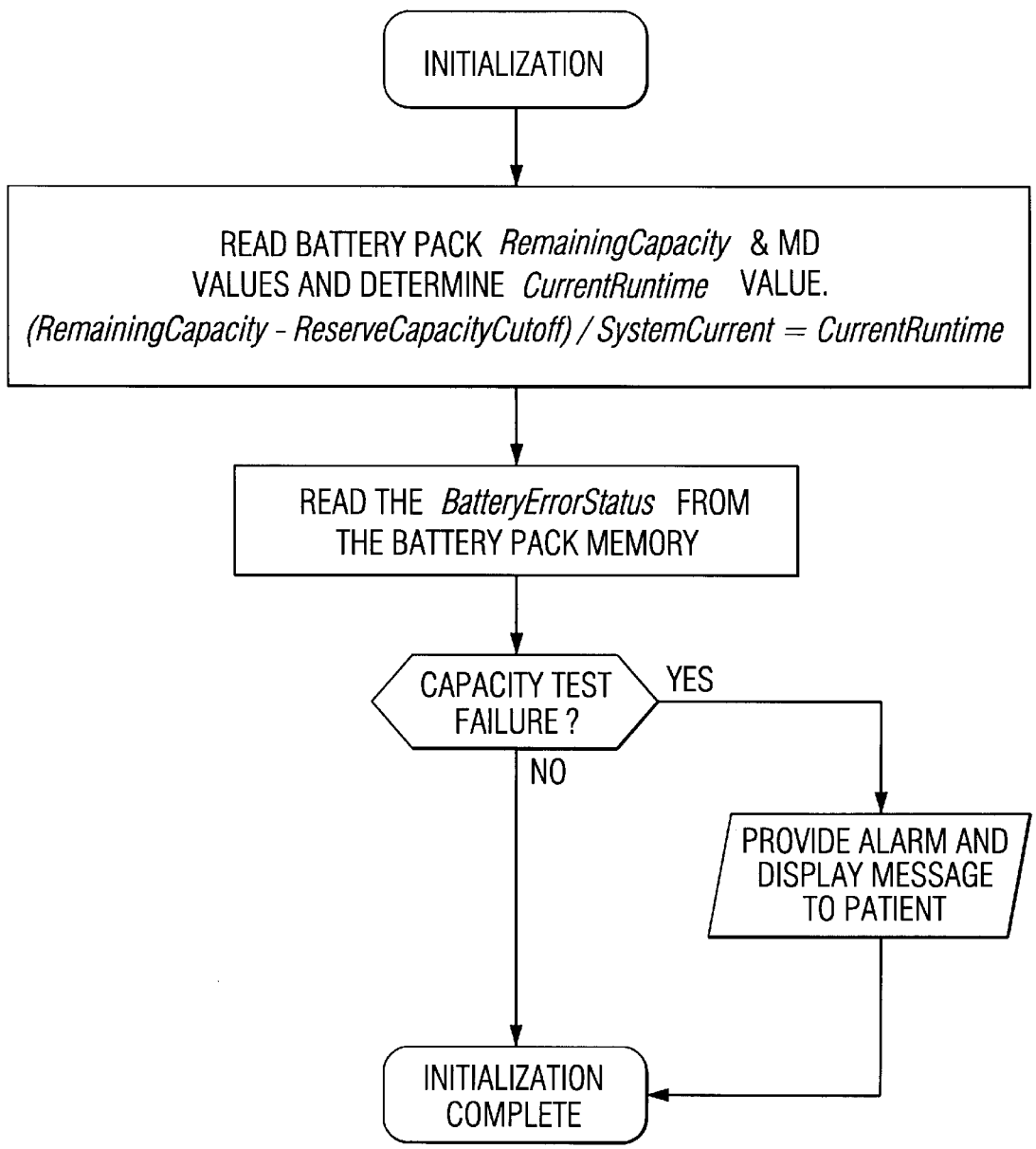
FIG. 8 is a flow diagram illustrating a presently preferred initialization method.
Figure 9:
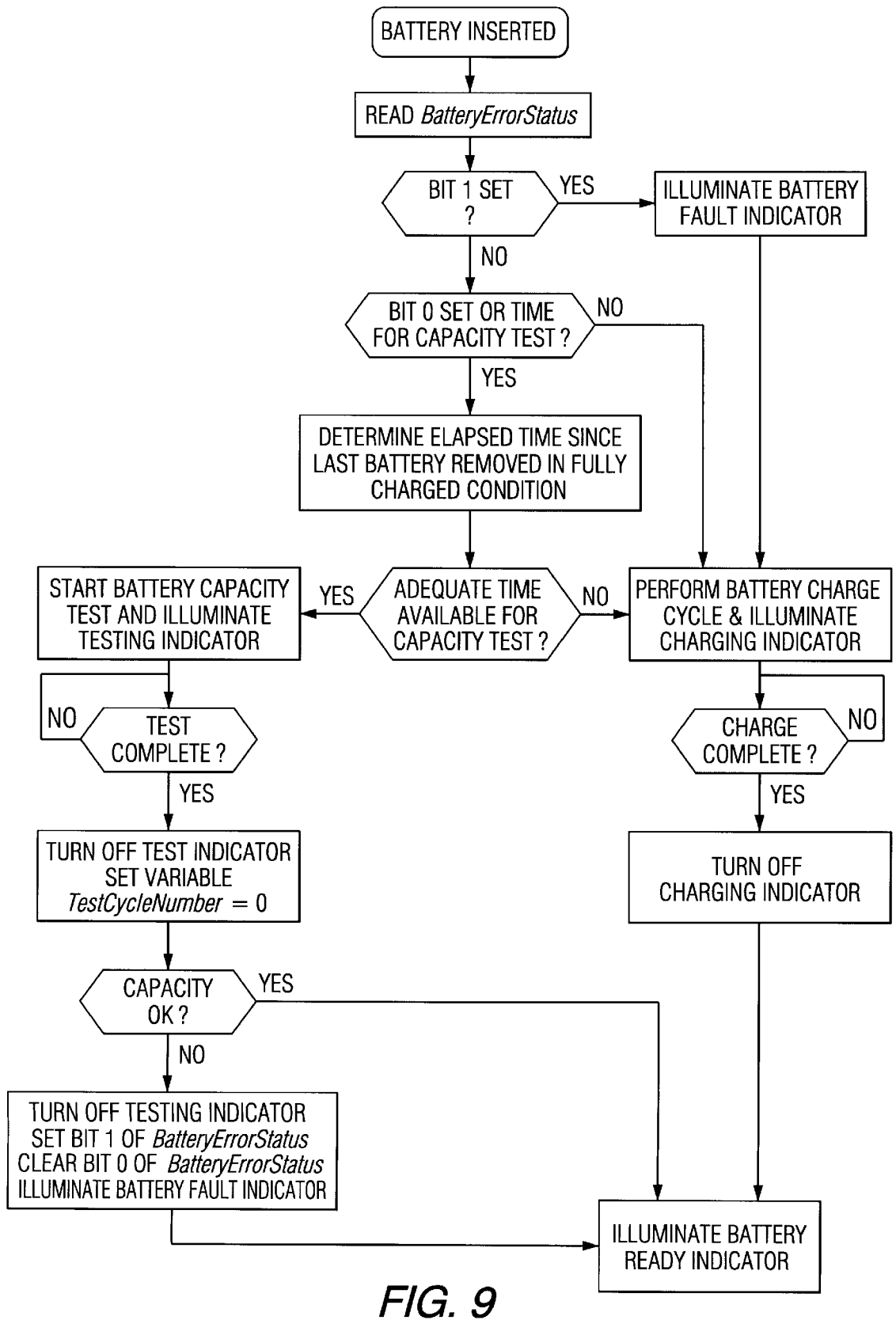
FIG. 9 is a flow diagram illustrating a presently preferred battery operation method.

Described below are certain software interface and data structures which can preferably be used in the smart battery interface. FIGS. 8 and 9 illustrate certain preferred flow diagrams which can be used as a guide during the design and implementation of both the battery charger 190 and monitor-defibrillator 112 software.

Determination and Adjustment of Monitor-Defibrillator Available Run Time

The determination of available monitor-defibrillator 112 run time is based upon multiple factors. The design of the monitor-defibrillator smart battery pack 118 preferably includes a BenchMarq™ Model BQ2092 "gas gauge" integrated circuit. The BQ2092 continuously monitors the current being consumed by the monitor-defibrillator 112 and adjusts an internal capacity register. The monitor-defibrillator 112 reads the capacity register to determine available operating time which is displayed to the patient in hours and minutes. The smart battery pack 118 internal circuitry has been designed to particularly monitor the current being drawn by the data storage/processor circuitry of the monitor-defibrillator 112. However, the current drain caused by operation of the high voltage converter (approximately 8 amps) is not monitored by the BenchMarq gas gauge. Even if it were, the conventional internal circuitry could not measure the current drain with the desired precision. Due to this, the monitor-defibrillator 112 can have, for example, the aforementioned energy monitoring circuit 180 for precisely measuring this current drain and using this information to make an appropriate adjustment to the smart battery pack 118 gas gauge, based on measuring the operation time of the converter. The remaining capacity register of the smart battery pack 118 will be adjusted based on a calculation performed by the monitor-defibrillator 112 after operation of the converter.

Additionally, due to the design of the monitor-defibrillator 112, the remaining capacity register contained in the BenchMarq BQ2092 IC does not provide enough information to accurately determine the remaining run time of the monitor-defibrillator 112. The monitor defibrillator 112 design specifications indicate that the monitor-defibrillator 112 must be able to operate for a period of 24 hours, and at the end of the 24 hour period, be able to deliver five full energy defibrillation pulses without entering converter foldback mode. Converter foldback mode is a mode of converter operation that is enabled if the battery pack terminal voltage falls below a predefined threshold during operation of the converter interface. As a result of this specification, the smart battery pack 118 must have sufficient reserve capacity to operate the converter interface while maintaining a battery pack voltage which is above this threshold. Due to the five pulse requirement, the smart battery pack 118 must have additional calibration information stored in the battery pack memory which allows the monitor-defibrillator 112 to verify that sufficient reserve capacity exists in the battery to operate the converter at the 24 hour operating point.

A reserve battery capacity calibration constant, "ReserveCapacityCutoff," will be stored in each monitor-defibrillator 112 during manufacturing. The value of ReserveCapacityCutoff must be determined by a battery qualification test which exercises the smart battery pack 118 under simulated current drawings. The monitor-defibrillator 112 software will read this constant during initialization and use it to determine run time based on the following formula:

(RemainingCapacity−ReserveCapacityCutoff)÷SystemCurrent= CurrentRuntime.

In the above formula, the constants ReserveCapacityCutoff and SystemCurrent must be maintained in the monitor-defibrillator 112 data storage/processor 22. The battery pack 118 will also maintain a RemainingCapacity (command code 0x0F) register which will be used to determine available operating time and which is adjusted by circuitry internal to the battery pack 118 based on actual sensed battery current drain. The monitor-defibrillator 112 software generally decrements its run time counter in a linear fashion. In one method, adjustments to the run time, outside of a straight decrement in time, will only be made if the above calculation indicates a run time less than the decremented time amount or operation of the high voltage converter occurs time amount or operation of the high voltage converter occurs. However, in a presently preferred method, the monitor-defibrillator 112 predicts the amount of operating time remaining based on actual usage. The current drain of the system is measured by hardware/software in the monitor-defibrillator 112, this is in addition to the smart battery pack 118, and averaged over a defined interval. When the run time value is needed, e.g. the patient pressing the display button or a periodic system low battery check, the monitor-defibrillator 112 will calculate the estimated run time amount based on the RemainingCapacity value that is maintained in the smart battery pack 118 and the average current consumption measured by the RemainingCapacity (0x0F) register. This run time value is a more realistic prediction of how long the system will operate based on actual usage. The only time the smart battery pack 118 RemainingCapacity register value is adjusted by the monitor-defibrillator 112, is during converter operation. If an adjustment becomes necessary, the monitor-defibrillator 112 will modify the battery pack 118 RemainingCapacity (0x0F) register with a new capacity value based on the duration of converter operation.

When a battery pack 118 is initially inserted into the monitor-defibrillator 112, the above formula will be used to initialize the initial run time variable CurrentRuntime. The Current/Runtime variable is decremented based on elapsed time after the initial calculation is performed.

Periodically, the monitor-defibrillator 112 will recalculate the formula and compare the calculated run time to the run time which is being decremented based upon elapsed time. If the new calculated run time indicates less time available than the CurrentRuntime variable, the variable will be set equal to the calculated time. This situation may occur if the patient display is activated for significant periods of time, causing greater than average current drain from the battery.

Monitor Defibrillator Battery Initialization Sequence

The flow diagram shown in FIG. 8 illustrates one presently preferred embodiment of software flow during initialization of the monitor-defibrillator 112 when a battery pack 118 is installed. The initial calculation of CurrentRuntime is performed along with a test for charger detected error conditions. A status variable, "BatteryErrorStatus," maintained in the battery pack is shared by the monitor-defibrillator 112 and charger. Variable BatteryErrorStatus, located in the battery pack 118 ManufacturerAccess (Command code 0x00) register low byte, is used by the monitor-defibrillator 112 to flag the battery charger 190 to perform a capacity test cycle after certain operating conditions are detected such as converter foldback or a low battery voltage state. Detected error conditions and resulting battery charger 190 operations are described later in this document.

Battery Capacity Testing and General Charger Functionality

In addition to basic battery charging sequences, the battery charger 190 can conduct periodic battery capacity measurements and monitor the integrity of the battery pack 118. The battery pack 118 capacity test will be initiated based on checking an internal battery pack register value, "TestCycleNumber," that will be stored in the ManufacturerAccess (Command code 0x00) register high byte of the BQ2092. Variable TestCycleNumber is reset to zero by the charger 190 whenever a battery capacity test cycle has been completed. This value is maintained and updated by the charger 190 whenever the battery pack 118 completes a charge cycle. Manufacturing constant "CyclesPerTestSequence" will be stored in the manufacturing data (command code 0x23) area of the BenchMarq BQ2092 IC. Constant CyclesPerTestSequence will be programmed at the time of manufacturing and will indicate the number of charge cycles between capacity test sequences.

When a smart battery pack 118 is inserted into the charger 190, the charger 190 will read variables TestCycleNumber and CyclesPerTestSequence and determine if a capacity test cycle is required. Prior to commencement of the capacity test it will be necessary for the charger 190 to determine if the patient's current battery pack 118 is capable of sustaining monitor-defibrillator 112 operations for the duration of the test. The battery charger 190 will not initiate a battery capacity test sequence if the previously charged battery pack 118 has Bit 1 of the BatteryErrorStatus set or does not have sufficient reserve capacity to operate the monitor-defibrillator 112 for the duration of the test.

As mentioned in the previous section, it is also possible that the monitor-defibrillator 112 may periodically request a battery capacity test via variable BatteryErrorStatus Bit 0 contained in the BenchMarq BQ2092 ManufacturerAccess (Command code 0x00) register low byte. The following details the bit positions in BatteryErrorStatus and their meaning.

BatteryErrorStatus (Low Byte of ManufacturerAccess (0x00)

Bit 0: Set by the monitor-defibrillator 112 if converter foldback or low battery voltage condition exists during operation.

Bit 1: Set by battery charger if the smart battery pack 118 fails battery capacity test or the battery pack 118 is otherwise defective.

If the battery charger 190 detects that Bit 0 of BatteryErrorStatus is set, the charger 190 should proceed to perform a battery capacity test. The charger 190 must keep track of the time when a fully charged battery pack 118 was removed from the charger 190 and assume that it will power the monitor-defibrillator 112 system for a period of twelve hours. The decision to perform the battery capacity test must take into consideration the actual worst case duration of the test and the remaining run time of the last fully charged battery pack 118. The test should not be initiated if the battery pack 118 which is currently being used by the patient does not have sufficient reserve capacity to power the monitor-defibrillator 112 for the worse case capacity test time or if the battery pack 118 is faulty (Bit 1 is set).

Upon completion of the capacity test, the charger 190 should compare the measured battery capacity to battery pack 118 parameter LowLimitCapacity which is stored in the manufacturing data area. If the battery pack 118 capacity is less than this value, the charger 190 should clear Bit 0 & set Bit 1 of variable BatteryErrorStatus. If the test passes, then both error Bits should be cleared.

The flow diagram shown in FIG. 9 illustrates one general, presently preferred, method of operation of the battery charger 190. When a smart battery pack 118 is removed from the system or not installed, all status illuminators should be turned off.

Mapping of Defined Variables to BQ2092 Memory

The previously defined battery maintenance constants will be mapped into the manufacturing data area and the variables mapped to the registers of the BQ2092. This section defines the storage locations of the variables and constants in the BQ2092. The variables and constants must be initialized to default values during the battery pack manufacturing process.

| Constant Name | Size in Bytes | Manufacturing String Index |
| --- | --- | --- |
| Low Limit Capacity | 2 | BASE ADDRESS+0&1 |
| CyclesPerTestSequence | 1 | BASS ADDRESS+2 |
| Variable Name | Size in Bytes | Register Location in BenchMarq BQ2092 |
| BatteryErrorStatus | 1 | ManufacturerAccess(0x00) Low Byte |
| TestCycleNumber | 1 | ManufacturerAccess(0x00) High Byte |

Regarding the manufacturing string address, the base address indicates the first byte of the manufacturing data string provided by BQ2092 function ManufacturingData (command code 0x23).

In accordance with the patent statutes we have described principles of operation and preferred embodiments of our invention. It should be understood, however, that within the scope of the appended claims, the invention may be practiced in a manner other than as illustrated and described.

What is claimed is:

1. A battery management system for a portable patient worn electronic energy delivery device for monitoring and administering therapy for a treatable heart condition, the battery management system comprising:
   a. a portable electronic device having a data storage/processor, a receptacle for a rechargeable battery pack, and portable electronic device maintenance circuitry for providing an indication of the operating condition of the portable electronic device;
   b. a rechargeable battery pack removably received in said receptacle, said battery pack having a memory/processor for monitoring and storing an operational condition of the battery pack;
   c. said portable electronic device data storage/processor adapted to exchange information with said battery pack memory/processor regarding said operational condition of said battery pack;
   d. said portable electronic device having energy monitoring circuitry which monitors at least energy consumption during a high voltage operation of said portable electronic device such as when administering said therapy for a treatable heart condition; and
   e. said portable electronic device updating said operational condition of said battery pack.

2. The battery management system of claim 1 further comprising said battery pack memory/processor continuously monitoring energy consumption by at least said portable electronic device data/storage processor and maintenance circuitry and correspondingly updating said operational condition of said battery pack stored in said memory/processor.

3. The battery management system as recited in claim 2 wherein said data storage/processor further comprises a data processing portion for determining available device operating time before said battery pack requires recharging.

4. The battery management system as recited in claim 3 wherein data corresponding to at least one of abnormally high current draw, normal current draw during an elapsed time period, device fault conditions, depletion of battery capacity during non-use, and said operational condition of said battery pack is stored by said data storage/processor, and wherein said data processing portion uses said data in determining said available device operating time.

5. The battery management system as recited in claim 4 further comprising:
   a. said data corresponding to patient initiated energy usage resulting from manual manipulation of portable electronic device controls by the patient;
   b. said data processing portion analyzing said energy usage over a time interval to determine a pattern of such patient initiated energy usage; and
   c. said data processing portion adjusting said available operating time responsive to said analyzing to predict a more accurate available operating time by accounting for predictable future patient initiated energy usage.

6. The battery management system as recited in claim 5 further comprising a portable electronic device display operatively associated with said data processing portion, said available device operating time displayed by said portable electronic device display.

7. The battery management system as recited in claim 1 further comprising a battery pack recharger, said recharger comprising:
   a. a processor for communicating with said battery pack memory/processor;
   b. power supply circuitry to provide a current for recharging said battery pack;
   c. a receptacle having contacts to operably receive said battery pack for recharging and transferring information between said recharger processor and said battery pack memory/processor; and
   d. battery pack maintenance circuitry for providing an indication of the operating condition of said battery pack.

8. The battery management system as recited in claim 7 wherein said battery pack maintenance circuitry further comprises:
   a. circuitry to determine a charging condition of said rechargeable battery pack;
   b. circuitry to compare the charging condition with at least one predetermined parameter stored in said battery pack memory/processor; and
   c. circuitry to induce said power supply means to provide a charging current to said rechargeable battery pack when the comparing circuitry has determined the charging condition is below a predetermined level of at least one predetermined parameter.

9. The battery management system as recited in claim 1 wherein said portable electronic device comprises a monitor-defibrillator unit adapted to be worn by a patient for delivering electrical therapy to the heart of the patient upon the occurrence of a treatable heart arrhythmia, and said data storage/processor has patient physiological data stored therein.

10. The battery management system as recited in claim 9 wherein said monitor-defibrillator unit further comprises an input/output interface such at an external device can input patient background data to said data storage/processor.

11. The battery management system as recited in claim 10 wherein input/output interface permiits said patient physiological data to be at least one of retrieved from said data storage/processor by an external device and transmitted to a remote location.

12. The battery management system as recited in claim 1 wherein said portable electronic device further comprises circuitry for at least one of permitting data to be retrieved from said data storage/processor by an external device and transmitted to a remote location.

13. The battery management system as recited in claim 7 wherein said data storage/processor comprises circuitry for storing manufacturing data for the portable electronic device, said manufacturing data including at least one of the following:
   a. device serial number;
   b. rechargeable battery pack serial number;
   c. rechargeable battery pack expiration date; and
   d. a permissible number of rechargeable battery pack recharges.

14. The battery management system as recited in claim 13 wherein said portable electronic device further comprises a real time clock for providing an indication of actual date and time and means for comparing said actual date and time with said battery pack expiration date, and means for providing an alarm if said actual date and time exceeds said rechargeable battery pack expiration date.

15. The battery management system as recited in claim 14 wherein said portable electronic device further comprises a back-up power source operatively associated with said real time clock independent of said power supply circuitry.

16. The battery management system as recited in claim 7 wherein said battery pack recharger further comprises test circuitry for testing the operation of said rechargeable battery pack, said test circuitry comprising:

a. circuitry to discharge the battery pack to a predetermined starting level;

b. circuitry to recharge the battery pack to a predetermined charging level; and c. circuitry to perform a load test on said battery pack to determine the integrity of said battery pack.

17. The battery management system as recited in claim 16 wherein said recharger processor further comprises:

a. a counter to count the number of times said power supply circuitry provides current to said battery pack;

b. circuitry to compare said permissible number of battery pack recharges with the number of times counted by said counter; and c. circuitry to provide a second alarm if the number of times counted by said counter is equal to said permissible number of battery pack recharges.

18. The battery management system as recited in claim 1 further comprising:

a. said data storage/processor having a data processing portion, said data processing portion determining available device operating time before said battery pack requires recharging;

b. said data storage/processor having a data storage portion wherein there is stored data corresponding to at least one of abnormally high current draw, normal current draw during an elapsed time period, device fault conditions, and depletion of battery pack capacity during non-use, and wherein said data processing portion utilizing said data stored in said data storage portion in determining said available device operating time;

c. a patient display operatively associated with said data processing portion to display said available device operating time; and d. an alarm associated with at least one of said data processing portion and said patient device display, said alarm notifying a patient of said available device operating time.

19. The battery management system as recited in claim 1 wherein said personal electronic device further comprises:

a. voltage converter for storing energy from said battery pack; and b. a controller operatively associated with said voltage converter and said battery pack, said controller further comprising:

i. circuitry to determine an energy condition of said voltage converter, said energy condition including at least an insufficient energy condition wherein there is insufficient energy to both deliver a treatment to the patient and preserve operating data;

ii. circuitry to determine a voltage condition of said battery pack, said voltage condition including at least an inadequate voltage condition wherein the battery capacity is inadequate for reliable operation of the portable electronic device;

iii. circuitry responsive to at least one of said inadequate voltage condition and said insufficient energy condition to one of operate said voltage converter in a low current mode and terminate operation of said voltage converter, and iv. a discharge circuit responsive to said inadequate energy condition for discharging said voltage converter; and c. an alarm operatively associated with said controller, said alarm notifying the patient whether the personal electronic device can provide treatment based on said converter energy condition and said voltage condition, and wherein said alarm is at least one of an audible message and a visual display on a portable electronic device display.

20. The battery management system as recited in claim 1 wherein said personal electronic device further comprises:

a. a controller operatively associated with said battery pack, said controller operating said personal electronic device in a low current mode when said portable electronic device is not performing necessary system operating functions;

b. said controller further having circuitry to determine a voltage condition of said battery pack, said voltage condition including at least an inadequate voltage condition wherein said battery pack capacity is inadequate for reliable operation of said portable electronic device and wherein said controller does not supply power to said personal electronic device responsive to said inadequate voltage condition; and c. a digital to analog converter operatively associated with said controller, said controller able to power down said analog to digital converter to conserve energy when not in use.

21. The battery management system as recited in claim 1 wherein said personal electronic device further comprises:

a. voltage converter to store energy from said battery pack;

b. controller operatively associated with said voltage converter and said battery pack, said controller further comprising:

i. circuitry to determine an energy condition of said voltage converter;

ii. circuitry to determine a voltage condition of said battery pack; and iii. circuitry to perform a load test on said battery pack for testing high current capability thereof; and c. an analog to digital converter operatively associated with said controller and said analog to digital converter for use in monitoring stored battery energy.

22. The battery management system as recited in claim 3 wherein said data processing portion further comprises an analog to digital converter.

23. The battery management system as recited in claim 22 further comprising powering down said analog to digital converter when not being used to conserve power to conserve power.

24. The battery management system as recited in claim 1 wherein said portable electronic device further comprises:

a. a controller operatively associated with said battery pack; and b. a voltage converter for storing energy from said battery pack.

25. The battery management system as recited in claim 24 wherein said controller comprises:

a. circuitry to determine a converter energy condition of said voltage converter, said converter energy condition including at least an insufficient energy condition wherein there is insufficient energy to both deliver a treatment to the patient and preserve operating data;

b. circuitry to determine a battery voltage condition of said battery pack, said battery voltage condition including at least an inadequate voltage condition wherein said battery pack capacity is inadequate for reliable operation of said portable electronic device;

c. circuitry responsive to at least one of said inadequate voltage condition and said insufficient energy condition to one of operate said voltage converter in a low current mode and terminate operation of said voltage converter; and d. discharge circuit responsive to said insufficient energy condition to discharge said voltage converter.

26. The battery management system as recited in claim 25 further comprising an alarm operatively associated with said controller for notifying a patient whether said personal electronic device can provide sufficient energy for treatment based on said converter energy condition and said battery voltage condition.

27. The battery management system as recited in claim 26 wherein said alarm further comprises at least one of an audible message and a visual message via a personal electronic device display.

28. The battery management system as recited in claim 25 wherein said controller further comprises an analog to digital converter for monitoring stored battery energy.

29. The battery management system as recited in claim 25 wherein said controller further comprises circuitry to perform a load test on said battery pack for testing high current capability of said battery pack.

30. A method for determining available operating time of a portable electronic device having a rechargeable battery pack, said portable electronic device having a data/storage processor for calculating said available operating time, said rechargeable battery pack having a memory/processor communicating with said data/storage processor, said method for determining available operating time comprising:

a. storing at least a first value in said battery pack memory/processor indicative of an operating condition of said battery pack;

b. storing at least a second value in said portable electronic device data storage/processor indicative of at least operating parameters of said portable electronic device; and c. determining said available operating time as a function of said first and second values.

31. The method of claim 30 further comprising:

a. said first value is a variable indicative of remaining battery capacity and continuously updating said first value responsive to changes in said remaining battery capacity due to energy consumption by said portable electronic device;

b. said second value is a pair of values, one being a battery calibration constant and the other being a constant representative of system current; and c. said available operating time being the difference between said remaining battery capacity and said battery calibration constant divided by said system current constant.

32. The method of claim 30 further comprising:

a. monitoring patient initiated energy usage resulting from manual operation of at least one of status and display functions of said portable electronic device;

b. analyzing said patient initiated energy usage over a time interval to determine a pattern of patient initiated energy usage; and c. adjusting said available operating time responsive to said pattern of patient initiated energy usage to more accurately predict said available operating time.

33. The method of claim 31 wherein said adjusting of said available operating time comprises decreasing said available operating time proportionally to a depletion of energy from said battery pack which would result if said patient initiated energy usage continued consistently with said pattern of patient initiated energy usage.

34. A battery management method for a recharging device for a rechargeable battery pack of a portable electronic device, said rechargeable battery pack having a memory/processor and said recharging device having a processor operably connected to said memory/processor, said battery management method comprising:

a. storing a first value in said battery pack memory/processor indicative of how many battery capacity tests said battery pack has been subjected to;

b. storing a second value in said battery pack memory/processor indicative of how many charge cycles said battery pack has been subjected to between said battery capacity tests;

c. storing a third value in said battery pack memory/processor indicative of a battery error condition;

d. reading said first, second and third values stored in said battery pack memory/processor;

e. determining whether a battery capacity test required based upon said first, second and third values; and f. performing a battery capacity test on said battery pack if required.

35. The method of claim 34 further comprising:

a. storing a fourth value in said battery pack memory/processor indicative of a low limit capacity of said battery pack;

b. performing said battery capacity test to measure prevailing battery capacity;

c. comparing said prevailing battery capacity to said low limit capacity; and d. updating said third value stored in said battery pack to indicate a battery error condition responsive to said prevailing battery capacity being less than said low limit capacity.

* * * * *

UNITED STATES PATENT AND TRADEMARK OFFICE
CERTIFICATE OF CORRECTION

PATENT NO. : 6,169,387 B1　　　　　　　　　　　　　　　　　　　　Page 1 of 1
DATED : January 2, 2001
INVENTOR(S) : Thomas E. Kaib It is certified that error appears in the above-identified patent and that said Letters Patent is hereby corrected as shown below:

<u>Column 23, claim 3,</u>
Line 33, change "2" to -- 1 --.

Signed and Sealed this

Nineteenth Day of February, 2002

Attest:

JAMES E. ROGAN
*Attesting Officer*　　　*Director of the United States Patent and Trademark Office*